(12) United States Patent
Isaacs et al.

(10) Patent No.: US 6,265,540 B1
(45) Date of Patent: Jul. 24, 2001

(54) TISSUE SPECIFIC PRODRUG

(75) Inventors: John T. Isaacs; Samuel R. Denmeade, both of Baltimore, MD (US); S. Brogger Christensen, Copenhagen (DK); Hans Lilja, Skanor (SE)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/081,707

(22) Filed: May 19, 1998

Related U.S. Application Data

(60) Provisional application No. 60/080,046, filed on Mar. 30, 1998, and provisional application No. 60/047,070, filed on May 19, 1997.

(51) Int. Cl.[7] .................................................. C07K 16/00
(52) U.S. Cl. ........................ 530/326; 530/327; 530/328; 530/329; 530/330
(58) Field of Search ................................... 530/326–330, 530/391.1, 391.7

(56) References Cited

U.S. PATENT DOCUMENTS

| 5,599,686 | 2/1997 | Defeo-Jones et al. ................. 435/23 |
| 5,741,821 | 4/1998 | Roufogalis et al. .................. 514/734 |
| 5,866,679 | 2/1999 | DeFeo-Jones et al. .............. 530/322 |

FOREIGN PATENT DOCUMENTS

| 9600503 A1 | 1/1996 | (WO) . |
| WO 99/02175 | 1/1999 | (WO) . |

OTHER PUBLICATIONS

Defeo–Jones et al., "Novel oliogopeptides for diagnosis and treatment of prostate cancer", 1996, Chem Abstr. vol. 124:220505.

Primary Examiner—Sheela Huff
(74) Attorney, Agent, or Firm—Fish & Richardson P.C.

(57) ABSTRACT

The invention provides novel peptide prodrugs which contain cleavage sites specifically cleaved by prostate specific antigen (PSA). These prodrugs are useful for substantially inhibiting the non-specific toxicity of a variety of therapeutic drugs. PSA is secreted by prostatic glandular cells. Upon cleavage of the prodrug by PSA, the therapeutic drugs are activated and exert their toxicity. Novel sesquiterpene-γ-lactones are also provided by the invention, and are designed to be linked to carrier moieties such as the peptides of the invention. Methods for treating cell proliferative disorders are also featured in the invention.

17 Claims, No Drawings

TISSUE SPECIFIC PRODRUG

CROSS REFERENCE TO RELATED APPLICATIONS

This application claims priority from U.S. Provisional Application Ser. No. 60/047,070, filed May 19, 1997, and U.S. Provisional Application Ser. No. 60/080,046, filed Mar. 30, 1998.

FIELD OF THE INVENTION

This invention relates generally to the targeted activation of biologically active materials to cells that produce prostate specific antigen (PSA) and more specifically to PSA-specific peptides that activate therapeutic drugs.

BACKGROUND OF THE INVENTION

There is currently no effective therapy for men with metastatic prostate cancer who relapse after androgen ablation, even though numerous agents have been tested over the past thirty years. Prolonged administration of effective concentrations of standard chemotherapeutic agents is usually not possible because of dose-limiting systemic toxicities.

Prostate specific antigen (PSA) is a 33,000 kDa single chain glycoprotein first characterized from human prostate tissue. PSA is synthesized and secreted as a unique differentiation product of the prostatic glandular cells, both from normal and cancerous cells. Low levels of PSA are detected in normal and cancerous breast tissue also.

PSA is a serine protease with extensive sequence identity to the glandular kallikreins. It has chymotrypsin-like substrate specificity. Major proteolytic substrates are gel-forming proteins in freshly ejaculated semen, semenogelin I (SgI) and semenogelin II (SgII), produced in the seminal vesicles. Other PSA substrates are extracellular matrix components fibronectin, laminin, insulin-like growth factor binding proteins, the single chain form of urokinase-type plasminogen activator, and parathyroid hormone-related protein. PSA is enzymatically active in the extracellular fluid of prostatic cancer while enzymatically inactivated in the blood serum.

Thapsigargin (TG) is an sesquiterpene-γ-lactone available by extraction from the seeds and roots of the umbelliferous plant *Thapsia garganica* L. Thapsigargin selectively inhibits the sarcoplasmic reticulum (SR) and endoplasmic reticulum (ER) $Ca^{2+}$-ATPase (SERCA) pump, found in skeletal, cardiac, muscle and brain microsomes. The apparent dissociation constant is 2.2 pM or less.

TG operates by what is believed to be a unique method of killing cells. TG induced inhibition of the SERCA pump leads to depletion of the ER $Ca^{2+}$ pool. This depletion apparently results in the generation of a signal, possibly from an ER-derived diffusible messenger, so that the plasma membrane is more permeable to extracellular divalent cations. The resulting influx of these cations is responsible for the death of cells.

TG is poorly soluble in water, does not possess cell specificity, and is able to kill quiescent Go cells. For these reasons, unmodified TG would be difficult to administer and deliver systemically without significant non-specific host toxicity.

SUMMARY OF THE INVENTION

The present invention provides a novel class of peptides that include amino acid sequences containing cleavage sites for prostate specific antigen (PSA) and other enzymes with the same activity and proteolytic specificity as PSA. A representative amino acid sequence is provided and includes Ser-Lys-Leu-Gln (SEQ ID NO: 1), analogs, derivatives and conservative variations thereof.

The invention also provides novel analogs of therapeutic sesquiterpene-γ-lactones, including derivatives of the thapsigargins. The thapsigargins are a group of natural products isolated from species of the umbelliferous genus Thapsia. The term thapsigargins has been defined by Christensen, et al., *Prog. Chem. Nat. Prod.*, 71 (1997) 130–165. These derivatives contain a means of linking the therapeutic drug to carrier moieties, including peptides and antibodies. The peptides and antibodies can include those which specifically interact with antigens including PSA. The interactions can involve cleavage of the peptide to release the therapeutic analogs of sesquiterpene-γ-lactones.

The invention also provides a therapeutic prodrug composition, comprising a therapeutic drug linked to a peptide which is specifically cleaved by PSA. The linkage substantially inhibits the non-specific toxicity of the drug, and cleavage of the peptide releases the drug, activating it or restoring its non-specific toxicity.

The invention also provides a method for treating cell proliferative disorders, including those which involve the production of PSA, in subjects having or at risk of having such disorders. The method involves administering to the subject a therapeutically effective amount of the composition of the invention. The invention also provides a method of producing the prodrug composition of the invention. In another embodiment, the invention provides a method of detecting PSA activity in tissue. In yet another embodiment, the invention provides a method of selecting appropriate prodrugs for use in treating cell proliferative disorders involving PSA-production.

The invention also provides a method for detecting a cell proliferative disorder associated with PSA production in a tissue of a subject, comprising contacting a target cellular component suspected of having a PSA associated disorder, with a reagent which detects enzymatically active PSA.

The invention also provides a method of determining PSA activity in a PSA-containing sample, comprising contacting the sample with a detectably labeled peptide which is specifically cleaved by PSA for a period of time sufficient to allow PSA to cleave the peptide, detecting the detectable label to yield a detection level, which is then compared to the detection level obtained by contacting the same detectably labeled peptide with a standard PSA sample of known activity.

The invention also provides a method of imaging soft tissue and/or bone metastases which produce PSA, comprising administering a lipophilic imaging label linked to a peptide F which is specifically cleaved by PSA to a subject having or suspected of having a PSA-associated cell proliferative disorder, allowing PSA to cleave the peptide, allowing the lipophilic imaging label to accumulate in the tissue and/or bone, allowing the subject to clear the uncleaved peptide, and imaging the subject for diagnostic purposes. Unless otherwise defined, all technical and scientific terms used herein have the ordinary meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other reference materials mentioned herein are incorporated by reference in their entirety. In case of conflict, the present specification, including definitions, will control. In addition, the materials, methods, and examples are illustrative only and not intended to be limiting.

DETAILED DESCRIPTION

The invention provides a novel class of peptides that contain a cleavage site specific for prostate specific antigen (PSA). These peptides are efficiently and specifically cleaved by PSA. These peptides are useful for substantially inhibiting the non-specific toxicity of the therapeutic agents prior to the agents contacting a tissue containing PSA. The invention further provides novel sesquiterpene-γ-lactone analogs which can be linked to a variety of carrier moieties. The linkage substantially converts the derivative into an inactive prodrug. The prodrugs of the invention comprise peptide sequences containing a cleavage site specific for PSA, and therapeutic drugs. The compositions do not show significant non-specific toxicity, but in environments where PSA is found, the composition becomes activated when peptide is cleaved, releasing the therapeutic drug, which regains its non-specific toxicity.

PSA-Specific Peptide

As used herein, the term "prostate specific antigen" (PSA) means prostate specific antigen, as well as all other proteases that have the same or substantially the same proteolytic cleavage specificity as prostate specific antigen. As used herein, "sufficiently toxic" refers to therapeutic drugs which display nonspecific toxicity toward cells with an $LC_{50}$ concentration that is at least 3 times lower than the $LC_{50}$ concentration of the prodrugs of the invention, more preferably at least 20 times lower, and therapeutic drugs most preferably have an $LC_{50}$ concentration that is at least 100 times lower than the $LC_{50}$ concentration of the prodrugs of the invention. The term "contacting" refers to exposing tissue to the peptides, therapeutic drugs or prodrugs of the invention so that they can effectively inhibit cellular processes, or kill cells. Contacting may be in vitro, for example by adding the peptide, drug, or prodrug to a tissue culture to test for susceptibility of the tissue to the peptide, drug or prodrug. Contacting may be in vivo, for example administering the peptide, drug or prodrug to a subject with a cell proliferative disorder, such as prostate or breast cancer. By "polypeptide" is meant any chain of amino acids, regardless of length or post-translational modification (e.g., glycosylation or phosphorylation). As written herein, amino acid sequences are presented according to the standard convention, namely that the amino terminus of the peptide is on the left, and the carboxy terminus on the right. In one aspect, the invention features a peptide containing an amino acid sequence that includes a cleavage site specific for PSA or an enzyme having a proteolytic activity of PSA. The peptides of the invention are preferably not more than 20 amino acids in length, more preferably not more than amino acids in length. The preferred amino acid sequences of the invention are linear.

The cleavage site recognized by PSA is flanked by at least an amino acid sequence, $X_5X_4X_3X_2X_1$. This peptide contains the amino acid glutamine, asparagine or tyrosine at position $X_1$. $X_2$ can be leucine, tyrosine, or lysine. $X_3$ can be serine or lysine. $X_4$ can be serine, isoleucine, or lysine. $X_5$ can be from 0 to 16 further amino acids. Some preferred embodiments include a sequence for $X_5$ that is substantially identical to the 16 remaining amino acids in the wild type semenogelin I or semenogelin II sequence. The amino acid is sequence can further comprise $X_{-1}$ which is linked to the carboxy terminus of $X_1$ to create the amino acid sequence $X_5X_4X_3X_2X_1X_{-1}$. $X_{-1}$ is up to 10 further amino acids. Preferably, $X_{-1}$ has histidine, leucine, threonine or serine linked to the carboxy terminus of $X_1$. The PSA cleavage site is located at the carboxy terminal side of $X_1$, unless $X_{-1}$ has histidine linked to the carboxy terminus of $X_1$, in which case the PSA cleavage site is to the carboxy terminal side of histidine.

Another amino acid sequence is $X_6X_5X_4X_3X_2X_1$ in which $X_5$ is serine or lysine, $X_6$ is from 0 to 15 further amino acids, and the other amino acids are as above. $X_{-1}$ can also be present, as noted above. Another amino acid sequence is $X_6X_5X_4X_3X_2X_1$, in which $X_6$ is histidine or asparagine $X_7$ is from 0 to 14 further amino acids, and the other amino acids are as above. $X_{-1}$ can also be present, as noted above.

Some examples of preferred peptides include tetraamino acid sequences such as Ser-Lys-Leu-Gln (SEQ ID NO: 1), Ile-Ser-Tyr-Gln (SEQ ID NO: 2), and Lys-Ser-Lys-Gln (SEQ ID NO: 3). Some examples of referred pentaamino acid sequences are Ser-Ser-Lys-Leu-Gln (SEQ ID NO: 4), Lys-Ile-Ser-Tyr-Gln (SEQ ID NO: 5), and Thr-Lys-Ser-Lys-Gln (SEQ ID NO: 6). Some examples of preferred hexaamino acid sequences are His-Ser-Ser-Lys-Leu-Gln (SEQ ID NO: 7), Asn-Lys-Ile-Ser-Tyr-Gln (SEQ ID NO: 8), and Ala-Thr-Lys-Ser-Lys-Gln (SEQ ID NO: 9). Some examples of preferred heptaamino acid sequences are Glu-His-Ser-Ser-Lys-Leu-Gln (SEQ ID NO: 10), Gln-Asn-Lys-Ile-Ser-Tyr-Gln (SEQ ID NO: 11), and Glu-Asn-Lys-Ile-Ser-Tyr-Gln (SEQ ID NO: 12). As noted, further amino acids can comprise $X_{-1}$.

Further examples of the peptides of the invention are constructed as analogs of, derivatives of, and conservative variations on the amino acids sequences disclosed herein. Thus, the broader group of peptides having hydrophilic and hydrophobic substitutions, and conservative variations are encompassed by the invention. The term "isolated" as used herein refers to a peptide substantially free of proteins, lipids, nucleic acids, for example, with which it is naturally associated. Those of skill in the art can make similar substitutions to achieve peptides with greater activity and/or specificity toward PSA. For example, the invention includes the peptide sequences described above, as well as analogs or derivatives thereof, as long as the bioactivity of the peptide remains. Minor modifications of the primary amino acid sequence of the peptides of the invention may result in peptides which have substantially equivalent activity as compared to the specific peptides described herein. Such modifications may be deliberate, as by site-directed mutagenesis or chemical synthesis, or may be spontaneous. All of the peptides produced by these modifications are included herein, as long as the biological activity of the original peptide remains, i.e., susceptibility to cleavage by PSA.

Further, deletion of one or more amino acids can also result in a modification of the structure of the resultant molecule without significantly altering its biological activity. This can lead to the development of a smaller active molecule which would also have utility. For example, amino or carboxy terminal amino acids which may not be required for biological activity of the particular peptide can be removed. Peptides of the invention include any analog, homolog, mutant, isomer or derivative of the peptides disclosed in the present invention, as long as the bioactivity as described herein remains. All peptides were synthesized using L-amino acids; however, D-forms of the amino acids can be synthetically produced.

The peptides of the invention include peptides which are conservative variations of those peptides specifically exemplified herein. The term "conservative variation" as used herein denotes the replacement of an amino acid residue by another, biologically similar residue. Examples of conservative variations include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine, and threonine. The term "conservative variation" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention with respect to X positions which may be any of a number of amino acids. The peptides which are produced by such conservative variation can be screened for suitability of use in the prodrugs of the invention according to the methods for selecting prodrugs provided herein.

A wide variety of groups can be linked to the carboxy terminus of $X_1$ or $X_{-1}$. Notably, therapeutic drugs can be linked to this position. In this way, advantage is taken of the PSA-specificity of the cleavage site, as well as other functional characteristics of the peptides of the invention. Preferably, the therapeutic drugs are linked to the carboxy terminus either directly or through a linker group. The direct linkage is preferably through an amide bond, in order to utilize the proteolytic activity and specificity of PSA. If the connection between the therapeutic drug and the amino acid sequence is made through a linker, this connection is also preferably made through an amide bond, for the same reason. The linker may be connected to the therapeutic drug through any of the bond types and chemical groups known to those skilled in the art. The linker may remain on the therapeutic drug indefinitely after cleavage, or may be removed soon thereafter, either by further reactions with external agents, or in a self-cleaving step. Self-cleaving linkers are those linkers which can intramolecularly cyclize and release the drug, or undergo spontaneous $S_N1$ solvolysis and release the drug upon peptide cleavage. Such linkers are for example 2,2-dialkyl-2-(2-anisyl) acetic acid, described in Atwell et al., *J. Med. Chem.*, 37:371–380, (1994), and p-amidobenzyloxycarbonyl, described in Carl et al., *J. Med. Chem.*, 24:479–480, (1981). Further useful examples are provided in these references. Other materials such as detectable labels or imaging compounds can be linked to the peptide. Additionally, there can be up to 10 further amino acids at position $X_{-1}$. In certain embodiments, the amino acids linked to $X_1$ at this position are leucine, threonine, serine or histidine. Groups can also be linked to the amino terminus of $X_5$, including such moieties as antibodies, and peptide toxins, including the 26 amino acid toxin, melittin and the 35 amino acid toxin, cecropin B, for example. Both of these peptide toxins have shown toxicity against cancer cell lines. Such groups can also be attached to $X_4$ when $X_5$ is absent.

The length of the amino acid sequence plays a role in the ability of PSA to cleave the peptide, with at least a tetrapeptide required for activity. Tetrapeptides as recited above typically are not as soluble as hexapeptides, although PSA cleavage activity is similar. One skilled in the art will be able to readily identify specific groups to improve the water solubility of the peptides of the invention. Among the groups which should be considered are polysaccharides, including dextrans, cyclodextrins, starches and the like, including derivatives thereof. Therapeutic drugs which are water soluble may be linked to the peptides of the invention, thereby imparting water solubility to the complexes as a whole. The peptides of the invention may also contain conventional capping groups connected to the amino terminus of the peptide to prevent endopeptidase activity from degrading the peptide. Such capping groups include acetyl, succinyl, benzyloxycarbonyl, glutaryl, morpholinocarbonyl, and many others known in the art.

Amino acid sequences can be constructed that contain highly specific cleavage sites for PSA. The highly PSA-specific cleavage sites of the invention are cleaved by PSA to yield at least 5 picomoles of cleaved peptide per minute per 200 picomoles of PSA. Preferably, the peptides contain PSA-specific cleavage sites that yield at least 10 picomoles of cleaved peptide per minute per 200 picomoles of PSA. Most preferably, such cleavage sites yield at least 15 picomoles of cleaved peptide per minute per 200 picomoles of PSA.

Amino acid sequences can be constructed that are highly selective towards cleavage by PSA, so that cleavage by other purified extracellular proteases is minimized. Preferably, the peptides of the invention are cleaved by extracellular proteases other than PSA to yield not more than 4.0 picomoles of cleaved peptide per minute per 200 picomoles of purified extracellular non-PSA proteases. More preferably, the peptides are cleaved to yield not more than 2.0 picomoles of cleaved peptide per minute per 200 picomoles of purified extracellular non-PSA enzyme. Most preferably, not more than 2.0 picomole per minute of peptide are cleaved per 200 picomoles of purified extracellular non-PSA enzyme.

Highly PSA-specific amino acid sequences can be constructed that are also stable toward cleavage in sera. Preferably, the peptides containing this sequence yield at most 2.0 picomoles per minute of cleaved peptide in human serum. More preferably, the peptides containing this sequence yield at most 1.75 picomoles per minute of cleaved peptide in human serum. Most preferably, at most 1.5 picomoles per minute of cleaved peptide are yielded by enzymes found in human serum.

The preferred amino acid sequences of the invention are also highly selective towards cleavage by PSA as compared to purified intracellular proteases. Preferably, the peptides of the invention are cleaved by intracellular proteases other than PSA to yield not more than 35 picomoles of cleaved peptide per minute per 200 picomoles of purified intracellular protease. More preferably, the peptide do not yield more than 20 picomoles of cleaved peptide. Most preferably, not more than 5 picomoles of cleaved peptide are produced upon cleavage by purified intracellular proteases other than PSA. While not wishing to be bound by any particular theory, it is believed that essentially no pathogenic effects arise from cleavage of the peptides of the compositions of the invention through intracellular proteases, and that these proteases do not play a significant role in the activation of the therapeutic drugs of the invention. The peptides of the invention can be synthesized according to any of the recognized procedures in the art, including such commonly used methods as t-boc or fmoc protection of alpha-amino groups. Both methods involve stepwise syntheses whereby a single amino acid is added at each step starting from the C-terminus of the peptide. (see, Coligan, et al., *Current Protocols in Immunology,* Wiley Interscience, 1991, Unit 9). Peptides of the invention can also be synthesized by the well-known solid phase peptide synthesis methods described in Merrifield, *J. Am. Chem. Soc.,* 85:2149, 1962), and Stewart and Young, *Solid Phase Peptide Synthesis,* (Freeman, San Francisco, 1969, pp. 27–62), using a copoly (styrene-divinylbenzene) containing 0.1–1.0 mM amine/gram polymer. On completion of chemical synthesis, the peptides can be deprotected and cleaved from the polymer by treatment with liquid HF-10% anisole for about ¼ to 1 hour at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as solvent. Lyophilization of appropriate fractions of the column will yield the homogeneous peptide of peptide derivatives, which can then be characterized by such standard techniques as amino acid analysis, thin layer chromatography, high performance liquid chromatography, ultraviolet absorption spectroscopy, molar rotation, solubility, and quantitated by solid phase Edman degradation.

The invention encompasses isolated nucleic acid molecules encoding the PSA-specific peptides of the invention, vectors containing these nucleic acid molecules, cells harboring recombinant DNA encoding the PSA-specific peptides of the invention, and fusion proteins which include the PSA-specific peptides of the invention. Especially preferred are nucleic acid molecules encoding the polypeptides described herein.

Prodrug Compositions

The invention also features prodrug compositions which comprise a therapeutic drug linked to a peptide containing a cleavage site that is specific for prostate specific antigen or any enzyme which has the enzymatic activity of prostate specific antigen (PSA). As noted above, the peptides of the invention can be used to activate therapeutic drugs at PSA producing tissue. The peptides which are useful in the prodrugs of the invention are those described above.

The therapeutic drugs that may be used in the prodrugs of the invention include any drugs which can be directly or indirectly linked to the PSA-specifically cleavable peptides of the invention. Preferred drugs are those containing primary amines. The presence of a primary amine allows the formation of an amide bond between the drug and the peptide. This bond serves as the cleavage site for PSA. The primary amines may be found in the drugs as commonly provided, or they may be added to the drugs by chemical synthesis. The presence of the primary amine must allow the therapeutic drug to retain its non-specific toxicity when cleaved. Certain therapeutic drugs contain primary amines, for example, anthracycline antibiotics containing an amino sugar such as doxorubicin, daunorubicin, epirubicin (4-epidoxorubicin), idarubicin (4-demethoxydaunomycin) and the like. These drugs intercalate into polynucleotides and interfere with replication processes. Other therapeutic drugs are required to have primary amines introduced by chemical or biochemical synthesis, for example, sesquiterpene-γ-lactones such as those belonging to the guaianolide, inuchineolide, germacranolide, and eudesmanolide families of sesquiterpenoids. These include estafiatin, grossheimin, inuchinenolide, arglabin, thapsigargin and their derivatives, such as thapsigargicin and many others known to those skilled in the art. Thapsigargin and its derivatives are believed to act by inhibiting the SERCA pump found in many cells.

The peptide and therapeutic drug are linked directly or indirectly (by a linker) through the carboxy terminus of the amino acid at $X_1$ or $X_{-1}$. The site of attachment on the therapeutic drug must be such that the non-specific toxicity of the drug is substantially inhibited. Thus, the prodrug should not be significantly toxic. In other words, the $LC_{50}$ concentration of the therapeutic drug should be at least 5 times lower than the $LC_{50}$ concentration of the prodrugs of the invention, more preferably at least 20 times lower, and most preferably the $LC_{50}$ concentration of the therapeutic drug should be at least 100 times lower than the $LC_{50}$ concentration of the prodrugs of the invention.

In certain embodiments, the peptide and drug can be connected indirectly through a linker. The linker can either remain attached to the drug or be cleaved off. In embodiments in which the linker remains attached to the drug, the linker can be any group which does not substantially inhibit the non-specific toxicity of the drug after cleavage from the peptide. Suitable linkers are primary amine containing alkanoyl, alkenoyl, and arenoyl substituents. Examples of such linkers are CO—$(CH=CH)_{n1}$—$(CH_2)_{n2}$—Ar—$NH_2$, CO—$(CH_2)_{n2}$—$(CH=CH)_{n1}$—Ar—$NH_2$, CO—$(CH_2)_{n2}$—$(CH=CH)_{n1}$—CO—NH—Ar—$NH_2$ and CO—$(CH=CH)_{n2}$—$(CH_2)_{n1}$—CO—NH—Ar—$NH_2$ and substituted variations thereof, where n1 and n2 are from 0 to 5, and Ar is any substituted or unsubstituted aryl group. Substituents which may be present on Ar include short and medium chain alkyl, alkanoxy, aryl, aryloxy, and alkenoxy groups, nitro, halo, and primary secondary or tertiary amino groups, as well as such groups connected to Ar by ester or amide linkages. Amino acids can also serve as linkers.

In other embodiments, the linker is self-cleaving. Self-cleaving linkers are those which are disposed to cleave from the drug after the cleavage of the peptide by PSA. The linkers generally contain primary amines which form amide bonds to the carboxy terminus of the peptide sequence. The linkers can also contain a carboxylic acid which forms an amide bond to a primary amine found on the drug.

One method of linker self-cleavage relies on spontaneous $S_N1$ solvolysis of the linker, activated by the cleavage of the peptide by PSA. The cleavage of the amide bond between the peptide terminal carboxyl group and the primary amine on the linker releases π electron density into an aromatic system present in the linker, stabilizing the development of a positive charge developing on a carbon atom α to the aromatic system. This charge stabilization eliminates the carboxylic acid, which is subsequently hydrolyzed from the drug. Examples of self-cleaving linkers of this type include p-amidobenzyloxycarbonyl, and substituted derivatives which do not significantly detrimentally affect the stabilization of positive charge at the α carbon.

Another method of linker self-cleavage utilizes cyclization of aromatic amines substituted with alkanone groups which allow the formation of intramolecular cyclic structures utilizing the lone electron pair of the amine which attack an electrophilic carbon such as that of the carbonyl. Five and six membered rings are formed preferably from such cyclization. Useful examples include 2-(2-anisyl) acetic acids and 3-(2-anisyl) propionic acids, as well as acid derivatives. With respect to such derivatives, short chain alkyl groups such as methyl, ethyl are useful as substituents. Naphthalene derivatives such as 8-amino-1-naphthalenecarboxylic acid and 8-amino-1-naphthaleneacetic acid derivatives.

As outlined above, peptide cleavage frees the electrons of the amine, which attack the carbonyl carbon, allowing the drug (leaving group) to be released. The carboxy terminus of the peptide is attached to the primary amine group of the linker by an amide bond, and the primary amine of the drug is attached to the carboxylic acid group of the linker, also by an amide bond.

In such embodiments, the linker is not required to be non-interfering with the non-specific toxicity of the drug, as long as it is cleaved within a period of time short enough to allow the drug to remain localized where it has been activated, or within a period of time short enough to prevent inactivation by any means.

Preferably the prodrugs of the invention are not taken up by the cells, but are cleaved extracelullarly by PSA to yield at least 5 picomoles of therapeutic drug per minute per 200 picomoles of PSA. Preferably, the prodrugs yield at least 10 picomoles of cleaved drug per minute per 200 picomoles of PSA. Most preferably, at least 15 picomoles of cleaved drug per minute per 200 picomoles of PSA are produced.

Preferably, the prodrugs of the invention are cleaved by extracellular proteases other than PSA to yield not more than 4.0 picomoles of cleaved therapeutic drug per minute per 200 picomoles of purified extracellular non-PSA proteases. More preferably, the prodrugs are cleaved to yield not more than 2.0 picomoles of cleaved drug per minute per 200 picomoles of purified extracellular non-PSA enzyme. Most preferably, not more than 2.0 picomole per minute of prodrug are cleaved per 200 picomoles of purified extracellular non-PSA enzyme.

Preferably, the prodrugs of the invention yield at most 2.0 picomoles per minute of cleaved therapeutic drug in human serum. More preferably, the prodrugs yield at most 1.75 picomoles per minute of cleaved drug in human serum. Most preferably, at most 1.5 picomoles per minute of cleaved drug are yielded by enzymes found in human serum.

Preferably, the prodrugs of the invention are cleaved by intracellular proteases other than PSA to yield not more than 35 picomoles of cleaved drug per minute per 200 picomoles of purified intracellular protease. More preferably, the prodrugs do not yield more than 20 picomoles of cleaved drug. Most preferably, not more than 5 picomoles of cleaved drug are produced upon cleavage by purified intracellular proteases other than PSA. While not wishing to be bound by any particular theory, it is believed that essentially no pathogenic effects arise from cleavage of the peptides of the compositions of the invention through intracellular proteases, and that these proteases do not play a significant role in the activation of the therapeutic drugs of the invention.

The prodrugs of the invention may also comprise groups which provide solubility to the prodrug as a whole in the solvent in which the prodrug is to be used. Most often the solvent is water. This feature of the invention is important in the event that neither the peptide nor the therapeutic drug is soluble enough to provide overall solubility to the prodrug. These groups include polysaccharides or other polyhydroxylated moieties. For example, dextran, cyclodextrin, starch and derivatives of such groups may be included in the prodrug of the invention.

Sesquiterene-γ-lactone Analogs

The invention also features a derivatized sesquiterpene-γ-lactone analog, the derivatization including providing the molecule with a residue substituted with a primary amine. The primary amine can be used to link the derivatized sesquiterpene with various other moieties. Among these are peptides which link to the analog to give prodrugs without significant non-specific toxicity, but enzymatic reactions with PSA affords the toxic drug. These enzymatic reactions can liberate the non-specific toxic thapsigargin derivative, for example by cleavage through hydrolysis or proteolysis, various reactions of the side chains of the peptide, or other reactions which restore the non-specific toxicity of the sesquiterpene-γ-lactone derivative. These reactions can serve to activate the derivatized sesquiterpene locally gg at PSA-producing tissue, and with relative exclusivity to regions in which these enzymatic reactions take place. For example, if a derivatized sesquiterpene-γ-lactone analog is linked, via a primary amine, to a peptide containing an amino acid sequence which includes a PSA-specific cleavage site, the analog can be released from the peptide selectively in regions where PSA, or other enzymes having the proteolytic activity of PSA, is found. The primary amine can likewise be used to link a derivatized sesquiterpene-γ-lactone analog to an antibody which binds an epitope in the target tissue.

Among the sesquiterpene-γ-lactone analogs preferred for use in the present invention are those of the guaianolide, inuchineolide, germacranolide, and eudesmanolide families of sesquiterpene-γ-lactone analogs. These include estafiatin, grossheimin, inuchinenolide, arglabin, thapsigargin and their derivatives, such as thapsigargicin and many others known to those skilled in the art. One of the preferred class of analogs is that based on the thapsigargin structure.

Thapsigargin is a sesquiterpene-γ-lactone having the following molecular structure:

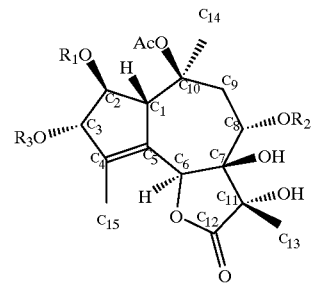

wherein $R_1$ and $R_2$ are substituents to be described below, and $R_3$ is an alkanoyl or alkenoyl substituent, preferably angeloyl ($CO—C(CH_3)=CHCH_3$).

Thapsigargin is an effective inhibitor of the $Ca^{2+}$ ion pump proteins of intracellular membranes located in sacroplasmic reticulum (SR) and endoplasmic reticulum (ER) of skeletal, cardiac, muscle and brain microsomes. As such, it displays a general non-specific toxicity toward many normal host cells. A method of targeting the proliferation independent cytotoxicity of thapsigargin selectively to cancer cells is needed. A number of thapsigargin analogs have been developed which can be coupled to enzymatically susceptible moieties. The analogs of the present invention include thapsigargin analogs that contain primary amines. The primary amines allow the coupling of thapsigargin analogs to appropriate moieties.

Referring to the thapsigargin skeleton, primary amines can be placed in substituent groups pendant from either the C-2 or the C-8 carbon. These positions are substituted with the groups —OR, and —$OR_2$ respectively in the thapsigargin structure shown above. These substituent groups can comprise primary amine-containing alkanoyl, alkenoyl or arenoyl substituents. Preferably, these substituent groups are represented by the following structures: unsubstituted or alkyl-, aryl-, halo-, alkoxy-, alkenyl-, amido- or amino-substituted $CO—(CH=CH)_{n1}—(CH_2)_{n2}—Ar—NH_2$, $CO—(CH)_{n1}—(CH=CH)_{n1}—Ar—NH_2$, $CO—(CH_2)_{n2}—(CH=CH)_{n1}—CO—NH—Ar—NH_2$ and substituted variations thereof, where n1 and n2 are from 0 to 5, Ar is any substituted or unsubstituted aryl group, and the position of $NH_2$ on Ar can be ortho, meta or para with respect to the position of the remainder of the substituent group.

Particularly preferred substituent groups are 6-(N-[3-amino-4-methylphenyl]-carboxamido)hexanoyl, 4-(N-[3-amino-4-methylphenyl]-carboxamido)butanoyl, 3-(N-[3-amino-4-methylphenyl]-carboxamido)propanoyl, 4-aminobenzoyl, 4-aminocinnamoyl, 3-[4-aminophenyl] propionoyl, 2-[4-aminophenyl]acetyl, and 4-[4-aminophenyl]butanoyl, 4-[4-aminophenyl]pentanoyl, 4-[4-aminophenyl] hexanoyl, 4-[4-aminophenyl] heptanoyl, or 4-[4-aminophenyl] ocanoyl substituents.

The primary amine-containing thapsigargin analogs as generally outlined above are synthesized by removing the 8-O-butanoyl group by triethylamine catalyzed methanolysis of thapsigargin. Attachment of anhydrides of dicarboxylic acids of various lengths affords analogs in which the acyl group attached to a 0-8 end in a free carboxylic acid. A dicyclohexylcarbodiimide (DCCI) promoted coupling of 2,4-diaminoarene to the carboxylic acid analogs yield primary aromatic amine-containing thapsigargin analogs. The primary amine is a potential coupling point for a number of moieties, including the peptide sequence of the invention, via the carboxyl terminus of the peptide.

The primary amine-containing thapsigargin analogs of the invention have non-specific toxicity toward cells. This toxicity is measured as the concentration of analog needed to kill 50% of clonogenic cells ($LC_{50}$). The $LC_{50}$ of the analogs of the invention is desirably at most 20 $\mu$M, preferably at most 5 $\mu$M, and more preferably at most 500 nM of analog.

The primary amine-containing thapsigargin analogs of the invention have endoplasmic reticulum $Ca^{2+}$-ATPase inhibitory activity. This activity is measured as the concentration of analog needed to inhibit 50% of this ATPase ($IC_{50}$). The $IC_{50}$ of the analogs of the invention is desirably at most 500 nM, preferably at most 200 nM, and more preferably at most 50 nM of analog.

Methods of Treatment Using Prodrugs

The invention also provides methods of treating PSA-producing cell proliferative disorders of the invention with the prodrugs of the invention.

The prodrugs of the invention and/or analogs or derivatives thereof can be administered to any host, including a human or non-human animal, in an amount effective to treat a disorder.

The prodrugs of the invention can be administered parenterally by injection or by gradual infusion over time. The prodrugs can be administered intravenously, intraperitoneally, intramuscularly, subcutaneously, intracavity, or transdermally. Preferred methods for delivery of the prodrug include intravenous or subcutaneous administration. Other methods of administration will be known to those skilled in the art.

Preparations for parenteral administration of a prodrug of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases, and the like.

The term "cell-proliferative disorder" denotes malignant as well as non-malignant cell populations which often appear to differ from the surrounding tissue both morphologically and genotypically. Malignant cells (i.e. cancer) develop as a result of a multistep process. The PSA-specific prodrugs of the invention are useful in treating malignancies of the various organ systems. Essentially, any disorder which is etiologically linked to PSA expression could be considered susceptible to treatment with a PSA-specific prodrug. One such disorder is a malignant cell proliferative disorder, for example. The term "therapeutically effective amount" as used herein for treatment of cell proliferative disorders refers to the amount of prodrug sufficient to cause a reduction in the number of unwanted cells. The term "therapeutically effective" therefore includes the amount of prodrug sufficient to prevent, and preferably reduce by at least 25%, and more preferably to reduce by 90%, the number of unwanted cells. The dosage ranges for the administration of prodrug are those large enough to produce the desired effect. Generally the dosage will vary with age, condition, sex, and extent of the disorder in the subject, and can be determined by one skilled in the art. The dosage can be adjusted by the individual physician in the event of any contraindications. In any event, the effectiveness of treatment can be determined by monitoring tumor ablation.

Method of Producing Prodrugs

The invention, in another aspect, provides a method of producing the prodrugs of the invention. This method involves linking a therapeutically active drug to a peptide of the invention. Such peptides are described above. After the drug and peptide are linked to produce a therapeutic prodrug composition, the non-specific toxicity of the drug is substantially inhibited. In certain embodiments, the peptide is linked directly to the drug. In other embodiments, the peptide is indirectly linked to the drug, the linkage occurring through a linker. In each case the carboxy terminus of the peptide is used for linking. That is, in an amino acid sequence $X_5X_4X_3X_2X_1$, the link is established through $X_1$. If $X_{-1}$ is linked to the carboxy terminus of $X_1$, the carboxy terminus of $X_{-1}$ is used for linking. The therapeutic drug contains a primary amine group to facilitate the formation of an amide bond with the peptide. Many acceptable methods of coupling carboxyl and amino groups to form amide bonds are known to those of skill in the art.

This bond is cleaved by PSA, releasing the therapeutic drug. Suitable linkers include any chemical group which contain a primary amine. The linkers for use in the present invention include amino acids, primary amine-containing alkyl, alkenyl or arenyl groups.

The connection between the linker and the therapeutic drug may be of any type known in the art, preferably covalent bonding. The linker group may remain attached to the therapeutic drug if its attachment does not significantly reduce the non-specific toxicity of the drug. In certain embodiments, the linker is a cleavable linker, which may be cleaved either by an external agent, or it may be a self-cleaving linker. External agents which may effect cleavage of the linker include enzymes, proteins, organic or inorganic reagents, protons and any other agents which do not affect the non-specific toxicity of the drug or prodrug.

In certain embodiments, the linker comprises an amino acid sequence. The sequence may be of any length, but is preferably between 1 and 10 amino acids, most preferably between 1 and 5 amino acids in length. Preferred amino acids are leucine, histidine, or amino acid sequences containing these amino acids, especially at their amino termini, although conservative variations of these amino acids may also be utilized.

Other groups may be added to the prodrugs of the invention, including those which render the prodrug soluble in water. These groups include polysaccharides or other polyhydroxylated moieties. For example, dextran, cyclodextrin and starch may be included in the prodrug of the invention.

Method of Screening Tissue

In another aspect the invention provides a method of detecting PSA-producing tissue using the peptides of the invention, as described above. The method is carried out by contacting a detectably labeled peptide of the invention with target tissue for a period of time sufficient to allow PSA to cleave the peptide and release the detectable label. The detectable label is then detected. The level of detection is then compared to that of a control sample not contacted with the target tissue. Many varieties of detectable label are available, including is optically based labels, such as chromophoric, chemiluminescent, fluorescent or phosphorescent labels, and radioactive labels, such as alpha, beta or gamma emitting labels. Examples of fluorescent labels include amine-containing coumarins such as 7-amino-4-methylcoumarin, 7-amino-4-trifluoromethyl, and other amine-containing fluorophores such as 6-aminoquinoline, and rhodamines, including rhodamine 110. Examples of radioactive labels include beta emitters such as $^{3}H$, $^{14}C$ and $^{125}I$. Examples of chromophoric labels (those that have characteristic absorption spectra) include nitroaromatic compounds such as p-nitroaniline. Examples of chemiluminescent labels include luciferins such as 6-amino-6-deoxyluciferin.

Preferably, the choice of detectable label allows for rapid detection and easily interpretable determinations. Detectable labels for use in the invention preferably show clearly detectable differences between detection from the cleaved and uncleaved state.

The invention provides a method for detecting a cell proliferative disorder which comprises contacting a PSA-specific peptide with a cell suspected of having a PSA-production associated disorder and detecting cleavage of the peptide. The peptide reactive with PSA is labeled with a compound which allows detection of cleavage by PSA. For purposes of the invention, a peptide specific for PSA may be used to detect the level of enzymatically active PSA in biological fluids and tissues such as saliva, blood, or urine. Any specimen containing a detectable amount of antigen can be used. The level of PSA in the suspect cell can be compared with the level in a normal cell to determine whether the subject has a PSA-production associated cell proliferative disorder. Preferably the subject is human.

Method of Screening Prodrugs

The invention also provides a method of selecting potential prodrugs for use in the invention. The method generally consists of contacting prodrugs of the invention with PSA-producing tissue and non-PSA producing tissue in a parallel experiment. "PSA-producing tissue" as used herein is tissue that produces at least 1 ng enzymatically active PSA/mL of fluid from tissue, or at least 1 ng of enzymatically active PSA/$10^6$ cells/24 hours from cells. The prodrugs which exert toxic effects in the presence of PSA-producing tissue, but not in the presence of non-PSA producing tissue are suitable for the uses of the invention. In other words, the $LC_{50}$ concentration of the prodrug in the presence of PSA-producing tissue is at least 3 times lower than the $LC_{50}$ concentration of the prodrug in the presence of non-PSA producing tissue, more preferably at least 20 times lower, and most preferably the $LC_{50}$ concentration of the prodrug in the presence of PSA-producing tissue is at least 100 times lower than the $LC_{50}$ concentration of the prodrug in the presence of non-PSA producing tissue.

Method of Determining PSA Activity

The invention also provides a method of determining the activity of PSA. The method generally consists of contacting detectably labeled prodrugs of the invention with samples may come from fluid drawn from PSA-producing tissue, from tissue culture media, from serum, saliva or urine, or any source which contains PSA. The cleavage of peptide which takes place by PSA results in the release of a detectable label, which is subsequently detected. This detection level is compared to the detection level which is found upon performing a parallel experiment in which the PSA-containing sample is a standard solution made up from purified PSA as described, for example, in Christensson, et al., Eur. J. Biochem. 194:755–765, (1990). This comparison results in a determination of the activity of the PSA which is present in the sample, given a correction for any differences in PSA concentration which may exist. Such correction may be accomplished directly by adjusting the concentrations of the standard and sample solutions to match each other or by mathematical correction means.

Method of Imaging Tissue

The invention in another aspect, provides a method of imaging soft tissue or bone metastases by providing peptides of the invention linked to lipophilic imaging labels that can be detected by imaging techniques, for example, positron emission tomography (PET). This method is accomplished generally by administering a peptide of the invention linked to a primary amine-containing lipophilic label to a subject having or suspected of having a PSA-producing associated cell proliferative disorder. The peptide is selectively cleaved from the lipophilic imaging label where enzymatically active PSA occurs in the subject (i.e., PSA producing tissues). The lipophilic imaging label is then drawn into the membranes of cells in the vicinity. After a period of time sufficient to allow cleavage of the peptide by PSA, and to allow the uncleaved peptide to be sufficiently cleared from the subject to allow reliable imaging, the subject is imaged. The lipophilic label accumulates in the soft tissue or bone that produces PSA, and allows a diagnosis of the subject. Suitable labels for PET scanning are radionuclides such as $^{18}F$, $^{11}C$, $^{13}N$ and 15O, and any other positron emitters known in the art. Lipophilicity can be engineered into the label by introducing the label into lipophilic fragments or moieties known to those in the art, by methods known to those skilled in the art.

The invention will be further described in the following examples, which do not limit the scope of the invention described in the claims.

EXAMPLES

The following examples illustrate the preparation and properties of certain embodiments of the invention.

Example 1

Peptide Cleavage by Purified Extracellular Proteases

The peptides discussed herein were custom synthesized by Enzyme Systems Products (Dublin, Calif.) and, after HPLC separation and purification to >95%, the molecular weights were confirmed by mass spectroscopy. All peptides had morpholinocarbonyl protecting the amino terminus and 7-amino-4-methylcoumarin (AMC) attached via an amide bond to the carboxyl group of the carboxy-terminal amino acid. Peptides were first dissolved in distilled water (5 mM) and then diluted into PSA assay buffer (50 mM Tris/0.1M NaCl pH 7.8). The glutamine-AMC peptide had the amino terminus and side chain amine unprotected and was obtained from Bachem (Torrance, Calif.).

PSA was purified from human seminal plasma as described in Christensson, et al. *Eur. J. Biochem.* 194:755–765, (1990). Plasmin, urokinase, tissue plasminogen activator (TPA), human plasma and porcine pancreatic kallikrein and α1-antichymotrypsin were obtained from Calbiochem (San Diego, Calif.). All other proteases were obtained from Sigma Chemical Co. (St. Louis, Mo.). Mouse serum was obtained from East Acres Biologicals (South Bridge, Mass.). Goat and calf sera were obtained from Gibco BRL (Grand Island, N.Y.). Rat serum was obtained in-house from sacrificed animals. Human serum was obtained from volunteers.

Table 1 displays the results of cleavage of various peptides linked to a fluorescent label, AMC (7-amino-4methylcoumarin). Cleavage was studied by measuring fluorescence change secondary to AMC release. Fluorescence detection was carried out with a Fluoroskan II 96 well fluorometric plate reader (ICN Biomedicals, Costa Mesa, Calif.), with excitation wavelength 355 nm and emission wavelength 460 nm. Data were collected and analyzed using Deltasoft III software (Biometallics, Princeton, N.J.). All reactions were performed at room temperature by the addition of substrate and proteases into PSA buffer, described below, in a final volume of 200 µL. The results were determined from the initial linear increase of fluorescence and were expressed as the picomoles of AMC released per minute based upon comparison to a standard curve of the fluorescence of known amounts of AMC (i.e., fluorescence was linear form 20 to 300 picomoles of AMC). The data were analyzed by Lineweaver-Burke reciprocal plots to determine the Michaelis-Menten constant (i.e., $K_m$) expressed as the amount of substrate needed to saturate half of the enzyme and the catalytic rate constant (i.e., $k_{cat}$) expressed as the amount of substrate converted to product per time per amount of enzyme.

Each assay contains 200 picomoles of the particular protease and 0.2 mM concentration of the particular substrate (i.e., 40,000 picomoles/200 µL of assay volume). The amino acid sequences expressed in one letter amino acid code represent the following amino acid sequences in the three letter amino acid code: EHSSKLQ (Glu-His-Ser-Ser-Lys-Leu-Gln)(SEQ ID NO: 10), QNKISYQ (Gln-Asn-Lys-Ile-Ser-Tyr-Gln)(SEQ ID NO: 11), ENKISYQ (Glu-Asn-Lys-Ile-Ser-Tyr-Gln)(SEQ ID NO: 12), and ATKSKQH (Ala-Thr-Lys-Ser-Lys-Gln-His)(SEQ ID NO: 13). Determinations listed in the table were carried out with substrates at 0.2 mM concentration in the PSA assay buffer (50 mM Tris/0.1M NaCl pH 7.8). The entry "UD" stands for "undetectable" and means that at most, 0.1 pmole of substrate cleavage per minute per 200 pmole protease took place. Asterisks represent experiments not performed. Abbreviations are as follows: PSA (prostate specific antigen), Chymo (chymotrypsin), Urokin (urokinase), TPA (tissue plasminogen activator), Thromb (thrombin), Kallik (human kallikrein, hK1).

Example 2
Kinetic Parameters of PSA Peptides

The data in Table 2 are the results of kinetic experiments with the peptide substrates used in Example 1. Experimental details are found in Example 1.

TABLE 2

| PSA Substrate | $K_m$ (µM) | $K_{cat}$ (s$^{-1}$) | $K_{cat}/K_m$ (s$^{-1}$M$^{-1}$) |
|---|---|---|---|
| EHSSKLQ (SEQ ID NO: 10) | 1165 | 0.012 | 10.6 |
| HSSKLQ (SEQ ID NO: 17) | 470 | 0.011 | 23.6 |
| SKLQ (SEQ ID NO: 1) | 813 | 0.020 | 24.6 |
| ATKSKQH (SEQ ID NO: 13) | 1310 | 0.0091 | 6.9 |

The amino acid sequences expressed in one letter amino acid code represent the following amino acid sequences in the three letter amino acid code: EHSSKLQ (Glu-His-Ser-Ser-Lys-Leu-Gln) SEQ ID NO: 10), HSSKLQ (His-Ser-Ser-Lys-Leu-Gln) (SEQ ID NO: 7), SKLQ (Ser-Lys-Leu-Gln) (SEQ ID NO: 1), and ATKSKQQ (Ala-Thr-Lys-Ser-Lys-Gln-His) (SEQ ID NO: 13) Determinations listed in the table were carried out with substrates at 0.2 mM concentration in the PSA assay buffer (50 mM Tris/0.1M NaCl pH 7.8).

Example 3
Stability of PSA Substrates in Various Sera

Because the prodrug can be given systemically via the blood, it is useful to determine the stability of the substrates in sera from a variety of species. The results are presented in Table 3. The substrates and experimental details are found as described in Example 1.

TABLE 1

| Amino acid Sequence | Picomoles of substrate cleaved/minute/200 pmoles of indicated protease | | | | | | | | |
|---|---|---|---|---|---|---|---|---|---|
| | PSA | Chymo | Elastase | Trypsin | Urokin | Plasmin | TPA | Thromb | Kallik |
| EHSSKLQ (SEQ ID NO: 10) | 31.6 | UD | UD | UD | UD | UD | UD | UD | UD |
| QNKISYQ (SEQ ID NO: 11) | 16.8 | 9.0 | 9.0 | UD | * | UD | 0.4 | 0.4 | * |
| ENKISYQ (SEQ ID NO: 12) | 14.4 | 3.6 | 2.6 | 1.8 | UD | 0.6 | .04 | 0.3 | UD |
| ATKSKQH (SEQ ID NO: 13) | 16.0 | 38.8 | UD | UD | UD | UD | UD | 0.2 | UD |

TABLE 3

| | picomoles AMC released/minute | | | | | |
|---|---|---|---|---|---|---|
| Sequence | Human | Mouse | Rat | Fetal Calf | Calf | Goat |
| EHSSKLQ (SEQ ID NO: 10) | UD | 2.17 | 0.06 | UD | UD | UD |
| QNKISYQ (SEQ ID NO: 11) | 1.54 | 1.67 | 10.7 | 11.60 | UD | 5.54 |
| ENKISYQ (SEQ ID NO: 12) | 1.27 | 3.21 | 11.2 | 9.59 | UD | 3.18 |
| ATKSKQH (SEQ ID NO: 13) | UD | 0.60 | 4.31 | 1.19 | UD | 0.35 |

The amino acid sequences expressed in one letter amino acid code represent the following amino acid sequences in the three letter amino acid code: EHSSKLQ (Glu-His-Ser-Ser-Lys-Leu-Gln) (SEQ ID NO: 10), HSSKLQ (His-Ser-Ser-Lys-Leu-Gln) (SEQ ID NO: 7), SKLQ (Ser-Lys-Leu-Gln) (SEQ ID NO: 1), and ATKSKQH (Ala-Thr-Lys-Ser-Lys-Gln-His) (SEQ ID NO: 13) Determinations listed in the table were carried out with substrates at 0.2 mM concentration in the PSA assay buffer (50 mM Tris/0.1M NaCl pH 7.8). AMC is 7-amino-4-methylcoumarin. The human serum used was 100% for each assay. The entry "UD" stands for "undetectable", and means that not more than 0.01 picomole of substrate per minute was cleaved.

Example 4
PSA Substrate Cleavage by Purified Intracellular Proteases

A family of peptide substrates based upon the EHSSKLQ (SEQ ID NO: 10) sequence was assayed for activity for the intracellular proteases, and the results given in Table 4.

TABLE 4

| | picomoles of peptide cleaved/min/200 picomoles protease | | | | |
|---|---|---|---|---|---|
| amino acid sequence | PSA | Cath B | Cath C | Cath D | Esterase |
| EHSSKLQ (SEQ ID NO: 10) | 31.6 | 4.3 | UD | 2.2 | UD |
| HSSKLQ (SEQ ID NO: 17) | 62.7 | 17.3 | UD | 3.8 | UD |
| SKLQ (SEQ ID NO: 1) | 29.6 | 31.2 | UD | 6.4 | UD |
| KLQ | 0.4 | 87.0 | UD | * | UD |
| LQ | UD | 190 | UD | 20.0 | UD |
| Q | UD | 1.0 | UD | 1.1 | 0.9 |

The amino acid sequences expressed in one letter amino acid code represent the following amino acid sequences in the three letter amino acid code: EHSSKLQ (Glu-His-Ser-Ser-Lys-Leu-Gln) (SEQ ID NO: 10), The shorter sequences are formed by deleting amino acids from the amino terminal side of the sequence. Determinations listed in the table were carried out with substrates at 0.2 mM concentration in the PSA assay buffer (50 mM Tris/0.1M NaCl pH 7.8), except SKLQ (SEQ ID NO: 1), KLQ and LQ, which were carried out in 1.4% acetonitrile/buffer and Q-AMC which was carried out in 0.2% formic acid/buffer, at pH 7.8. The entry "UD" stands for "undetectable" and means that at most, 0.1 pmole of substrate cleavage per minute per 200 pmole protease took place. Asterisks represent experiments not performed. Abbreviations are as follows: PSA (prostate specific antigen), Cath B, C, D (Cathepsins, B, C, D), Esterase (porcine liver esterase).

Example 5
Preparation of Thaosigargin Analogs

The starting material for all the synthesized analogs is 8-O-debutanoylthapsigargin, which is easily available by triethylamine catalyzed methanolysis of thapsigargin. Removal of the butanoyl results in loss of cytotoxic activity with an $LD_{50}$ of >50 μM compared to <100 nM for thapsigargin. Anhydrides of dicarboxylic acids of various lengths afforded analogs in which the acyl group attached to the O-8 ended in a free carboxylic acid. A dicyclohexylcarbodiimide (DCCI) promoted coupling of a 2,4-diaminoarene to the carboxylic acid analogs affords the derivatives in which contain a primary aromatic amine as a potential coupling point for additional moeities.

Another type of thapsigargin derivative has been prepared by reacting 8-O-debutanoylthapsigargin with a 4-aminophenyl aliphatic carboxylic acid like 4-aminocinnamic acid, 3-(4-aminophenyl) propionic acid, or 4-(4-aminophenyl)butanoic acid in the presence of DCCI and 4-dimethylaminopyridine. The aromatic amino group had previously been coupled to a boc-protected a-amino acid like glutamine or leucine by standard techniques. After deprotection of the amino group by standard techniques the thapsigargin derivative can be coupled to the peptide.

The synthesis of thapsigargin analogs was performed generally as follows. Unless otherwise stated all reactions were performed at room temperature, and the mixtures filtered and concentrated in vacuo with column chromatography performed over silica gel 60, (0.040–0.063, Merck). Each structure was further proven by $^{13}C$ and $^1H$ NMR spectroscopy and mass spectrometry. The NMR spectra have been recorded on a AF200X Bruker spectrometer in deuterated solutions using tetramethylsilane as an internal standard. In all the spectra, the signal originating in the acetyl, angeloyl, butanoyl, and octanoyl residues have been found as previously reported (Christensen, et al. *Phytochemistry.* 23:1659–63, (1984)), and are not reported. The $^1H$ NMR spectra were recorded at 200 MHz. The signals of H-9' have, in many cases, been overlapped by signals from the a protons in the octanoyl residue. The $^{13}C$ NMR spectra were recorded at 50 MHz. In the $^{13}C$ NMR spectra the assignments of signals with similar chemical shift values might be interchanged. The signals originating in C-2 and C-6 are hidden by the signals of chloroform, but have been visualized in a few cases by recording the DEPT spectra. The small amounts of compounds available have in some cases precluded the observation of signals of poor intensities.

Example 6
Preparation of 8-O-{6-(N-[3-amino-4-methylphenyl]-carboxamido)hexanoyl}-8-O-debutanoylthapsigargin (PDT)

A solution of 8-O-debutanoylthapsigargin (103 mg, 0.177 mmol), pimelic acid (185 mg, 1.16 mmol), dicyclohexylcarbodiimide(233 mg, 1.15 mmol) and dimethylaminopyridine (100 mg, 0.71 mmol) in dichloromethane is left for 3 hours at room temperature. The reaction mixture was filtered and the filtrate washed twice with hydrochloric acid (0.5 M, 10 ml). The organic phase was concentrated and 8-O-{6-carboxyhexanoyl}-8-O-debutanoylthapsigargin (63 mg, 49%) isolated by repeated chromatography using an eluent consisting of toluene-ethyl acetate (6:1) added 1% of acetic acid, to which increasing amounts of ethyl acetate were added. A solution of 8-O-{6-carboxyhexanoyl}-8-O-debutanoylthapsigargin (52 mg, 72 μmol), 2,4-diaminotoluene (DAT) (75 mg, 635 μmol), and dicyclohexylcarbodiimide(27.3 mg, 132 μmol) in dichloromethane (6 ml) was left for 1 hour at room temperature. The mixture was filtered, and the filtrate concentrated in vacuo to give a residue from which 26 mg (43%) of PDT was isolated as a colorless amorphous powder by chromatography using an eluent consisting of toluene-ethyl acetate (9:1). MS FAB⁻ $^1H$ NMR (($CD_3$)$_2$CO) δ: guaianolide 4.38 (br, s, H-1), 5.52 (dd, J 4.0 and 3.2 Hz, H-2), 5.80 (br, q, J 3 Hz, H-3), 5.67 (m, H- 6), 5.70 (t, J 3.6 Hz, H-8), 3.02 (dd, J 15 and 3 Hz), 1.86 (br, s, H-15), 1.43 (s, H-13), 1.42 (s, H-14); diaminotoluene 2.00 (br, s, $CH_3$), 7.12 (d, J 2.0 Hz, H-2), 7.08 (d, J 8.2 Hz, H-5), 7.18 (dd, J 8.2 and 2.0 Hz, H-6), pimeloyl 2.25–2.35 (m, H-2 and H-6), 1.55–1.65 (m, H-3 and H-5), 1.35–1.40 (m, H-4). m/z 825 [M-H⁺].

Example 7
Preparation of 8-O-{4-(N-[3-amino-4-methylphenyl]-carboxamido)butanoyl}-8-O-debutanoylthapsigarg in (GDT)

A solution of 8-O-debutanoylthapsigargin (100 mg, 0.17 mmol), glutaric anhydride (400 mg, 3.5 mmol) and 4-dimethylaminopyridine (100 mg, 0.82 mmol) in methylene chloride (10 ml) was left for 21 hours at room temperature and filtered. The filtrate was added to 4 M hydrochloric acid (10 ml) and extracted twice with ethyl acetate (10 ml). The organic phase was concentrated in vacuo to give 320 mg of a residue from which 68 mg (58%) of 8-O-{4-carboxybutanoyl}-8-O-debutanoylthapsigargin was isolated by column chromatography using an eluent consisting of toluene-ethyl acetate-acetic acid (5:1:0.01), to which increasing amounts of ethyl acetate were added. $^1$H NMR (CDCl$_3$) δ: guanianolide 4.22 (br, s, H-1), 5.46 (br, t, J 2 Hz, H-2), 5.7–5.5 (br, H-3, H-8 and H-6), 2.95 (dd, J 15 and 3 Hz, H-9), 1.78 (br, s, H-15), 1.43 (s, H-13), 1.38 (s, H-14); glutaryl 2.2–2.4 (m, H-2 and H-4), 141.2 (C-4), 130.1 (C-5), 78.3 (C-71C-1 1), 66.2 (C-8), 37.9 (C-9), 84.2 (C-10), 78.5 (C-11/C-7), 176.3 (C-12), 15.6 (C-13), 21.8 (C-14), 12.5 (C-15); glutaroyl 171.2 (C-1), 33.4 (C-2), 20.5 (C-3), 31.6 (C-4). MS FAB$^-$ m/z 693 [M–H$^+$].

A solution of 8-O-{4-carboxybutanoyl}-8-O-debutanoylthapsigargin (14 mg, 20 μmol), 2,4-diaminotoluene (10 mg, 80 μmol), and dicyclohexylcarbodiimide(7.9 mg, 40 μmol) in methylene chloride (2 ml) was left for 2 hours at room temperature. The mixture was filtered, and the filtrate concentrated in vacuo to give a residue from which GDT (8 mg, 50%) was isolated as a colorless amorphous powder by chromatography using an eluent consisting of toluene-ethyl acetate (9:1) to which increasing amounts of ethyl acetate were added. $^1$H NMR (CDCl$_3$) δ: guaianolide 4.17 (br, s, H-1), 5.46 (br, t, J 2 Hz, H-2), 5.6–5.4 (br, H-3, H-8 and H-6), 2.80 (dd, J 15 and 3 Hz, H-9), 1.78 (br, s, H-15), 1.43 (s, H-13), 1.38 (s, H-14); diaminotoluyl 2.00 (br, s, CH$_3$), 7.03 (d, J 2.0 Hz, H- 2), 6.90 (d, J 8.2 Hz, H-5), 6.72 (dd, J 8.2 and 2 Hz, H-6); glutaryl 2.2–2.4 (m, H-2 and H-4), 1.5–1.7 (m, H-3), 3C NMR (CDCl$_3$) o: The guanianolide nucleus 57.6 (C-1), 83.4 (C-3), 141.4 (C-4), 130.3 (C-5), 78.2 (C-7), 66.2 (C-8), 37.9 (C-9), 84.2 (C-10), 78.2 (C-11), 175.9 (C-12), 15.5 (C-13), 22.0 (C-15), 12.8 (C-15); glutaroyl 170.6 (C-1), 33.2 (C-2), 22.2 (C-3), 31.3 (C-4), 161.9 (C-5); diaminotolulyl 138.4 (C-1), 106.5 (C-2), 136.9 (C-3), 118.4 (C-4), 129.6 (C-5), 110.0 (C-6). MS FAB$^-$ m/z 797 [M–H$^+$].

Example 8
Preparation of 8-O-{3-(N-[3-amino-4-methylphenyl]-carboxamido)propanoyl}-8-O-debutanoylthapsigargin (SDT)

A solution of 8-O-{3-carboxypropanoyl}-8-O-debutanoylthapsigargin (25 mg, 33 μmol), 2,4-diaminotoluene (14 mg, 120 μmol), and dicyclohexylcarbodiimide(6 mg, 30 μmol) in methylene chloride (3 ml) was left for 4.5 hours at room temperature. The mixture was filtered and the filtrate concentrated in vacuo to give a residue from which SDT (8 mg, 33%) was isolated as a colorless amorphous powder by chromatography using an eluent consisting of toluene-ethyl acetate (9:1), to which increasing amounts of ethyl acetate were added. $^1$H NMR (CDCl$_3$) δ: guaianolide 4.20 (br s, H-1), 5.46 (br, t, J 2 Hz, H-2), 5.59 (br, t, H-8), 5.62 (br, H-3 and H-6), 2.92 (dd, J 15 and 3 Hz, H-9), 2.42 (dd, J 15 and 3 Hz, H-9'), 1.85 (br, s H-15), 1.40 (s, H-13), 1.38 (s, H-14); diaminotoluyl 1.95 (br, s, CH$_3$), 7.00 (d, J 2.0 Hz, H-2), 6.90 (d, J 8.0 Hz, H-5), 6.72 (dd, J 8 and 2.0 Hz, H-6); succinyl 2.68 (m, H-2 and H-3). $^{13}$C NMR (CDCl$_3$) δ: The guaianolide nucleus 57.6 (C-1), 83.4 (C-3), 141.4 (C-4), 130.1 (C-5), 78.6 (C-7), 67.1 (C-8), 38.1 (C-9), 84.6 (C-10), 176.0 (C-12), 15.9 (C-13), 22.6 (C-14), 12.9 (C-15); succinyl 172.6 (C-1), 29.1 (C-2), 29.0 (C-3), 167.1 (C-5); diaininotoluyl 138.8 (C-1), 136.4 (C-3), 119.7 (C-4), 127.4 (C-5), (C-2 and C-6 not seen). MS FAB$^-$ m/z 783 [M–H$^+$].

Example 9
Preparation of $^8$-O-(4-aminobenzoyl)-8-O-debutanoylthapsigargin (ABTD A solution of 8-O-debutanoylthapsigargin (52.9 mg, 91 μmol), boc protected 4-aminobenzoic acid (40 mg, 169 μmol), dicyclohexylcarbodiimide(24.5 mg, 122 μmol) and dimethylaminopyridine (7.3 mg, 60 μmol) in methylene chloride (5 ml) was left for 7 hours at room temperature. The solution was filtered and the filtrate was concentrated in vacuo. The residue was dissolved in a few ml of cold ethyl acetate and the solution filtered and concentrated in vacuo. ABT-boc (40.1 mg, 55%) was isolated as a colorless amorphous powder by chromatography using toluene-ethyl acetate (5:1) to which increasing amounts of ethyl acetate were added as an eluent followed by chromatography over silanized silica gel 60 RP 2 (0.070–0.230 mm, Merck) using methanol-water (9:1) as an eluent. $^1$H NMR (CDCl$_3$) δ: guaianolide 4.20 (br, s, H-1), 5.50 (br, t, J 2 Hz, H-2), 5.8–5.85 (H-3 and H-6), 5.72 (H-8), 3.14 (dd, J 15 and 3 Hz, H-9), 2.45 (dd, J 15 and 3 Hz, H-9'), 1.87 (br, s, H-15), 1.48 (s, H-13), 1.42 (s, H-14); 4-aminobenzoyl 7.85 (H-2 and H-6), 7.42 (11-3 and H-5); boc 1.52 (CH$_3$). $^{13}$C NMR (CDCl$_3$) δ: The guaianolide nucleus 57.2 (C-1), 84.0 (C-3), 141.2 (C-4), 130.2 (C-5), 78.6 (C-7), 67.1 (C-8), 38.1 (C-9), 84.5 (C-10), 78.5 (C-11), 175.6 (C-12), 15.9 (C-13), 22.5 (C-14), 12.9 (C-15); 4-aminobenzoyl 165.4 (C=O), 123.6 (C-1), 130.9 (C-2 and C-6), 117.6, (C-3 and C-5), 138.6 (C-4); boc 28.1 (CH$_3$), 81.3 (C—O), 152.2 (C=O). MS FAB$^-$ m/z 798 [M–H$^+$].

A solution of 8-O-(4-t-butoxycarbonylaminobenzoyl)-8-O-debutanoylthapsigargin (18.1 mg, 23 μM) and trifluoroacetic acid (TFA) (100 μl) in methylene chloride (2 ml) was then left for 3.5 hours at room temperature and concentrated in vacuo. ABT (14.0 mg, 88%) was isolated from the residue as a yellow amorphous powder by column chromatography using an eluent consisting of toluene-ethyl acetate-acetic acid (4:1:0.01) to which increasing amounts of ethyl acetate were added. $^1$H NMR (CDCl$_3$) δ: guaianolide 4.32 (br, s, H-1), 5.51 (br, t, J 2 Hz, H-2), 5.8–5.85 (H-3, 11-6 and H-8), 3.10 (dd, J 15 and 3 Hz, H-9), 2.48 (dd, J 15 and 3 Hz, H-9'), 1.88 (br, s, H-15), 1.48 (s, H-13), 1.45 (s, H-14); 4-aminobenzoyl 7.72 (H-2 and H-6), 6.60 (H-3 and H-5). $^{13}$C NMR (CDCl$_3$) δ: The guaianolide nucleus 57.2 (C-1), 83.9 (C-3), 141.4 (C-4), 130.1 (C-5), 79.1 (C-7), 66.8 (C-8), 38.3 (C-9), 84.5 (C-10), 79.0 (C-11), 175.2 (C-12), 16.3 (C-13), 23.3 (C-14), 12.9 (C-15); 4-aminobenzoyl 163.6 (C=O), 118.3 (C-1), 131.8 (C-2 and C-6), 113.8, (C-3 and C-5), 151.3 (C-4). MS FAB$^-$ m/z 698 [M–H$^+$].

Example 10
Preparation of 8-O-(4aminocinnamoyl)-8-O-debutanoylthapsigargin (ACT)

A solution of 8-O-debutanoylthapsigargin (62.1 mg, 107 μmol), boc protected 4-aminocinnamic acid (69.7 mg, 265 μM), dicyclohexylcarbodiimide(21.3 mg, 106 μM) and dimethylaminopyridine (12.8 mg, 106 μM) in dichloromethane (5 ml) was left for 3 hours at room temperature. The solution was filtered and the filtrate was evaporated in vacuo. The residue was dissolved in a few ml of cold ethyl acetate and the solution filtered and concentrated in vacuo to give a yellowish foam. ACT-boc (31.5 mg, 36%) was isolated as a white amorphous powder by chromatography using toluene-ethyl acetate (5:1) to which increasing amounts of ethyl acetate were added as an eluent followed by chromatography over silanized silica gel 60 RP 2 (0.070–0.230 mm, Merck) using methanol-water (9:1) as an eluent. $^1$H NMR (CDCl$_3$) δ: guaianolide 4.31 (br, s, H-1), 5.51 (br, t, J 2 Hz, H-2), 5.65–5.8 (H-3, H-6, and H-8), 3.08 (dd, J 15 and 3 Hz, H-9), 2.40 (dd, J 15 and 3 Hz, H-9'), 1.87 (br, s, H-15), 1.48 (s, H-13), 1.28 (s, H-14); 4-aminocinnamoyl 6.28 (d, J 16 Hz, H-α), 7.59 (d, J 16 Hz, H-β), 7.42 (H-2 and H-6), 7.28 (H-3 and H-5); boc 1.50 (CH$_3$). $^{13}$C NMR (CDCl$_3$) δ: The guaianolide nucleus 57.4 (C-1), 84.0 (C-3), 141.4 (C-4), 130.2 (C-5), 78.6 (C-7), 66.7 (C-8), 38.1 (C-9), 84.5 (C-10), 78.6 (C-11), 175.4 (C-12), 15.7 (C-13), 22.5 (C-14), 12.9 (C-15); 4-aminocinnamoyl 166.4 (C=O), 117.7 (C-α), 140.7 (C-β), 131.1 (C-1), 127.4 (C-2 and C-6), 118.2, (C-3 and C-5), 139.6 (C-4); boc 28.2 (CH$_3$), 81.9 (C—O), 152.3 (C=O). MS FAB$^-$ m/z 824 [M–H$^+$].

A solution of 8-O-(4t-butoxycarbonylaminocinnamoyl)-8-O-debutanoylthapsigargin (65.5 mg, 79 mM) and trifluoroacetic acid (TFA) (0.7 ml) in methylene chloride (7 ml) was then left for 0.25 hours at room temperature and concentrated in vacuo. ACT (45.1 mg, 78%) was isolated from the residue as an amorphous powder by column chromatography using an eluent consisting of toluene-ethyl acetate-acetic acid (4:1:0.01) to which increasing amounts of ethyl acetate were added. $^1$H NMR (CDCl$_3$) δ guaianolide 4.32 (br, s, H-1), 5.48 (br, t, J 2 Hz, H-2), 5.65–5.8 (H-3, H-6 and H-8), 3.04 (dd, J 15 and 3 Hz, H-9), 2.40 (dd, J 15 and 3 Hz, H-9=), 1.89 (br, s, H-15), 1.50 (s, H-13), 1.48 (s, H-14); 4-aminocinnamoyl 6.18 (d, J 16 Hz, H-a), 7.58 (d, J 16 Hz, H-b), 7.32 (H-2 and H-6), 6.63 (H-3 and H-5). $^{13}$C NMR (CDCl$_3$) δ The guaianolide nucleus 57.3 (C-1), 84.1 (C-3), 141.1 (C-4), 130.2 (C-5), 78.6 (C-7), 66.8 (C-8), 38.2 (C-9), 84.5 (C-10), 78.5 (C-11), 175.6 (C-12), 15.9 (C-13), 23.5 (C-14), 12.5 (C-15); 4-aminocinnamoyl 167.0 (C=O), 112.4 (C-a), 149.0 (C-b), 124.2 (C-1), 130.0 (C-2 and C-6), 115.0, (C-3 and C-5), 146.0 (C-4). MS FAB$^-$ m/z 748 [M–H$^+$].

Example 11
Preparation of 8-O-(3-[4-aminophenyl]propionyl)-8-O-debutanoylthapsigargin (APM)

A solution of 8-O-debutanoylthapsigargin (29.3 mg, 51 μmol), boc protected 3-aminophenyl propionic acid (30.2 mg, 114 μM), dicyclohexylcarbodiimide(14.2 mg, 71 μM) and dimethylaminopyridine (7.3 mg, 60 μM) in dichloromethane (2 ml) was left for 3 hours at room temperature. The solution was filtered and the filtrate was evaporated in vacuo. The residue was dissolved in a few ml of cold ethyl acetate and the solution filtered and concentrated in vacuo to give a residue, from which APT-boc (30 mg, 72%) was isolated as a colorless amorphous powder by chromatography using toluene-ethyl acetate (5:1) to which increasing amounts of ethyl acetate were added as an eluent. $^1$H NMR (CDCl$_3$) δ: guaianolide 4.20 (br, s, H-1), 5.39 (br, t, J 2 Hz, H-2), 5.5–5.6 (H-3, H-6, and H-8), 2.92 (dd, J 15 and 3 Hz, H-9), 1.75 (br, s, H-15), 1.33 (s, H-13), 1.28 (s, H-14); 4-aminophenylpropionyl 2.81 (br, t, J 7.5 Hz, H-α), 2.51 (br, t, J 7.5 Hz, H-β), 7.19 (H-2 and H-6), 7.02 (H-3 and H-5); boc 1.42 (CH$_3$). $^{13}$C NMR (CDCl$_3$) δ: The guaianolide nucleus 57.4 (C-1), 76.8 (C-2), 84.0 (C-3), 141.2 (C-4), 130.3 (C-5), 77.7 (C-6), 78.4 (C-7), 66.2 (C-8), 38.0 (C-9), 84.6 (C-10), 78.3 (C-11), 175.7 (C-12), 15.7 (C-13), 22.5 (C-14), 12.8 (C-15); 4-aminophenylpropionyl 171.9 (C=O), 36.1 (C-α), 29.6 (C-β), 134.8 (C-1), 128.6 (C-2 and C-6), 119.2, (C-3 and C-5), 136.3 (C-4); boc 28.2 (CH$_3$), 80.5 (C—O), 153.0 (C=O). MS FAB$^-$ m/z 826 [M–H$^+$].

A solution of 8-O-(3-[4-t-butoxycarbonylaminophenyl] propionyl)-8-O-debutanoylthapsigargin (40.5 mg, 49 mM) and trifluoroacetic acid (TFA) (0.4 ml) in methylene chloride (4 ml) was then left for 0.75 hours at room temperature and concentrated in vacuo. APT (33.7 mg, 96%) was isolated from the residue as an amorphous powder by column chromatography using an eluent consisting of toluene-ethyl acetate-acetic acid (4:1:0.01) to which increasing amounts of ethyl acetate were added. $^1$H NMR (CDCl$_3$) δ: guaianolide 4.25 (br, s, H-1), 5.48 (br, t, J 2 Hz, H-2), 5.55–5.7 (H-3, H-6 and H-8), 2.85 (dd, J 15 and 3 Hz, H-9), 1.75 (br, s, H-15), 1.28 (s, H-13), 1.23 (s, H-14); 4-aminophenylpropionyl 2.71 (br, t, J 7 Hz, H-a), 2.45 (br, t, J 7 Hz, H-b), 6.95 (d, J 7 Hz, H-2 and H-6), 6.65 (d, J 7 Hz, H-3 and H-5). $^{13}$C NMR (CDCl$_3$) d: The guaianolide nucleus 57.6 (C-1), 76.2 (C-2), 84.0 (C-3), 141.4 (C-4), 130.1 (C-5), 77.7 (C-6), 78.4 (C-7), 66.2 (C-8), 38.3 (C-9), 84.5 (C-10), 78.4 (C-11), 175.6 (C-12), 15.7 (C-13), 22.5 (C-14), 12.9 (C-15); 4-aminophenylpropionyl 172.0 (C=O), 36.3 (C-a), 29.8 (C-b), 131.0 (C-1), 129.1 (C-2 and C-6), 116.1, (C-3 and C-5), 143.4 (C-4). MS FAB$^-$ m/z 726 [M–H$^+$].

Example 12
Preparation of N-t-boc Protected 8-O-(3-[N-leucyl-4-aminophenyl]propionyl)-8-O-debutanoylthapsigargin (L-APT-boc)

A solution of 8-O-debutanoylthapsigargin (182 mg, 310 μmol), boc protected 3-(4-N-leucylaminophenyl)propionic acid (182 mg, 490 μmol), dicyclohexylcarbodiimide(72.8 mg, 350 μmol) and dimethylaminopyridine (45.5 mg, 60) in dichloromethane (10 ml) was left for 24 hours at room temperature. The solution was filtered and the filtrate was evaporated in vacuo. The residue was dissolved in a few ml of cold ethyl acetate and the solution filtered and concentrated in vacuo to give a residue, from which the title compound (57 mg, 19%) was isolated as a colorless amorphous powder by chromatography over silanized Silica gel using methanol-water (4:1) as an eluent. $^1$H NMR (CDCl$_3$) δ: guaianolide 4.26 (br, s, H-1), 5.47 (br, t, J 2 Hz, H-2), 5.7–5.7 (H-3, H-6, and H-8), 2.99 (dd, J 15 and 3 Hz, H-9), 1.83 (br, s, H-15), 1.37 (s, H-13), 1.33 (s, H-14); 4-aminophenylpropionyl 2.86 (br, t, J 7.5 Hz, H-α), 2.54 (br, t, J 7.5 Hz, H-β), 7.33 (H-2 and H-6), 6.99 (H-3 and H-5); boc 1.39 (CH$_3$); leucyl 4.33 (m, H-2), 1.6 m (H-3), 1.73 (m, H-4), 0.96 and 0.93 (two d, J 6.5, CH$_3$). $^{13}$C NMR (CDCl$_3$) δ: The guaianolide nucleus 57.8 (C-1), 77.0 (C-2), 84.3 (C-3), 141.5 (C-4), 130.6 (C-5), 77.9 (C-6), 78.6 (C-7), 66.5 (C-8), 38.3 (C-9), 84.8 (C-10), 78.6 (C-11), 176.3 (C-12), 15.8 (C-13), 22.6 (C-14), 12.9 (C-15); 4-aminophenylpropionyl 172.0 (C=O), 36.2 (C-α), 29.8 (C-β), 136.3 (C-1), 128.7 (C-2 and C-6), 120.5, (C-3 and C-5), 136.3 (C-4); boc 28.4 (CH$_3$), 80.6 (C—O), 156.7 (C=O); leucyl 172.4 (C=O), 53.9 (C-2), 40.9 (C-3), 22.7 and 23.0 (two CH$_3$). MS FAB$^-$ m/z 941 [M–H$^+$].

Example 13
Preparation of N-t-boc Protected 8-O-(3-[N-glutaminoyl-4-aminophenyl]propionyl)-8-O-debutanoylthapsigargin (Q-APT-boc)

A solution of 8-O-debutanoylthapsigargin (90.9 mg, 160 μmol), boc protected 3-(4-N-glutaminoylaminophenyl) propionic acid (91.6 mg, 230 μmol), dicyclohexylcarbodiimide (62.0 mg, 310 μmol) and dimethylaminopyridine (38.8 mg, 0.31 mmol) in dichloromethane (4 ml) was left for 7 hours at room temperature. The solution was filtered and the filtrate was evaporated in vacuo. The residue was dissolved in a few ml of cold ethyl acetate and the solution filtered and concentrated in vacuo to give a residue, from which the title compound (37 mg, 24%) was isolated as a colorless amorphous powder by chromatography using toluene-ethyl acetate (1:1) to which increasing amounts of ethyl acetate was added as an eluent. $^1$H NMR (CDCl$_3$) δ: guaianolide 4.30 (br, s, H-1), 5.45 (br, t, J 2 Hz, H-2), 5.7–5.6 (H-3, H-6, and H-8), 2.95 (dd, J 15 and 3 Hz, H-9), 1.80 (br, s, H-15), 1.30 (s, H-13), 1.30 (s, H-14); 4-aminophenylpropionyl 2.85 (br, t, J 7.5 Hz, H-α), 2.78 (br, t, J 7.5 Hz, H-β), 7.40 (H-2 and H-6), 7.06 (H-3 and H-5); boc 1.40 ($CH_3$); glutaminoyl 4.35 (m, H-2), 2.10 m (H-3), 2.30 (m, H-4). $^{13}C$ NMR ($CDCl_3$) δ: The guaianolide nucleus 57.5 (C-1), 84.0 (C-3), 141.1 (C-4), 130.7 (C-5), 77.7 (C-6), 78.5 (C-7), 66.5 (C-8), 38.0 (C-9), 84.7 (C-10), 78.5 (C-11), 176.1 (C-12), 15.7 (C-13), 20.4 (C-14), 12.8 (C-15); 4-aminophenylpropionyl 172.1 (C=O), 35.8 (C-α), 29.5 (C-β), 135.9 (C-1), 128.8 (C-2 and C-6), 120.7, (C-3 and C-5), 136.6 (C-4); boc 28.2 ($CH_3$), 80.3 (C—O), 156.4 (CO); glutaminoyl 171.0 (C=O), 54.0 (C-2), 28.9 (C-3), 28.9 (C-4), 176.8 (C=O). MS $FAB^-$ m/z 954.4462, calc. for $C_{49}H_{68}N_{68}O_{16}$ 954.4600

Example 14
Preparation of 8-O-(2-[4aminohenyl]acetyl)-8-O-debutanoylthapsigargin (AAT)

A solution of 8-O-debutanoylthapsigargin (60.0 mg, 100 μmol), boc protected 2-[4-aminophenyl] acetic acid (100.0 mg, 0.4 mM), dicyclohexylcarbodiimide(39.1 mg, 0.19 mM) and dimethylaminopyridine (23.0 mg, 0.19 mM) in dichloromethane (5 ml) was left for 1.5 hours at room temperature. The solution was filtered and the filtrate was evaporated in vacuo. The residue was dissolved in a few ml of cold ethyl acetate and the solution filtered and concentrated in vacuo to give a residue, from which AAT-boc (54.0 mg, 66%) was isolated as a colorless amorphous powder by chromatography using toluene-ethyl acetate (5:1) to which increasing amounts of ethyl acetate were added as an [el]uent. $^1H$ NMR ($CDCl_3$) δ: guaianolide 4.27 (br, s, H-1), 5.42 (t, J 2 Hz, H-2), 5.48 (br, s, H-3), 5.63 (br, s, H-6), 5.55 (br, s, H-8), 2.94 (dd, J 15 and 3 Hz, H-9), 2.20 (dd, J 15 and 3 Hz, H-9=), 1.80 (br, s, H-15), 1.38 (s, H-13), 1.18 (s, H-14); 4-aminophenylacetyl 7.30 (d, J 7 Hz, H-2 and H-6), 7.11 (d, J 7 Hz, H-3 and H-5), 3.55 (s, $CH_2$); boc 1.50 ($CH_3$). $^{13}C$ NMR ($CDCl_3$) δ: The guaianolide nucleus 57.4 (C-1), 76.7 (C-2), 84.1 (C-3), 141.4 (C-4), 130.3 (C-5), 77.6 (C-6), 78.4 (C-7), 66.7 (C-8), 37.9 (C-9), 84.7 (C-10), 78.4 (C-11), 176.1 (C-12), 15.9 (C-13), 22.5 (C-14), 12.8 (C-15); 4-aminophenylacetyl 171.1 (C=O), 130.7 (C-1), 130.2 (C-2 and C-6), 118.6, (C-3 and C-5), 137.5 (C-4), 40.9 ($CH_2$); boc 28.4 (CH), 80.7 (C—O), 153.1 (C=O). MS $FAB^-$ found 812.3879. Calculated for $C_{43}H_{58}NO_{14}$, 812.3857.

A solution of 8-O-(2-[4-t-butoxycarbonylaminophenyl] acetyl)-8-O-debutanoylthapsigargin (63.4 mg, 78 mM) and trifluoroacetic acid (TFA) (0.5 ml) in methylene chloride (5 ml) was then left for 3 hours at room temperature and concentrated in vacuo. APT (46.3 mg, 83%) was isolated from the residue as an amorphous powder by column chromatography using an eluent consisting of toluene-ethyl acetate-acetic acid (4:1:0.01) to which increasing amounts of ethyl acetate were added. $^1H$ NMR ($CDCl_3$) δ: guaianolide 4.26 (br, s, H-1), 5.43 (br, t, J 2 Hz, H-2), 5.52 (s, H-3 and H-8), 5.64 (s, H-6), 2.97 (dd, J 15 and 3 Hz, H-9), 2.20 (dd, J 15 and 3 Hz, H-9'), 1.82 (br, s, H-15), 1.34 (s, H-13), 1.21 (s, H-14); 4-aminophenylacetyl 6.98 (d, J 8 Hz, H-2 and H-6), 6.62 (d, J 8 Hz, H-3 and H-5), 3.47 (s, $CH_2$). $^{13}C$ NMR ($CDCl_3$) δ: The guaianolide nucleus 57.3 (C-1), 76.7 (C-2), 84.1 (C-3), 141.4 (C-4), 130.5 (C-5), 77.7 (C-6), 78.4 (C-7), 66.6 (C-8), 37.1 (C-9), 84.8 (C-10), 78.4 (C-1), 176.2 (C-12), 15.7 (C-13), 22.5 (C-14), 12.6 (C-15); 4-aminophenylacetyl 171.3 (C=O), 40.7 ($CH_2$), 131.0 (C-1), 130.5 (C-2 and C-6), 115.6, (C-3 and C-5), 141.4 (C-4). MS $FAB^-$ found 712.3347. Calculated for $C_{38}H_{51}NO_{12}$, 712.3333.

Example 15
Preparation of 8-O-(4-[4-aminohenl]butanoyl)-8-O-detbutanoylthapsigargin (ABuT)

A solution of 8-O-debutanoylthapsigargin (57.7 mg, 100 μmol), boc protected 4-[4-aminophenyl butanoic acid (63.3 mg, 0.23 mM), dicyclohexylcarbodiimide (25.8 mg, 0.12 mM) and dimethylaminopyridine (20.1 mg, 0.17 mM) in dichloromethane (3 ml) was left for 100 minutes at room temperature. The solution was filtered and the filtrate was evaporated in vacuo. The residue was dissolved in a few ml of cold ethyl acetate and the solution filtered and concentrated in vacuo to give a residue, from which ABuT-boc (81.5 mg, 97%) was isolated as a colorless amorphous powder by chromatography using toluene-ethyl acetate (2:1) to which increasing amounts of ethyl acetate were added as an eluent. $^1H$ NMR ($CDCl_3$) δ: guaianolide 4.25 (br, s, H-1), 5.42 (br, t, J 2 Hz, H-2), 5.5–5.6 (H-3, H-6 and H-8), 2.93 (dd, J 14 and 3 Hz, H-9), 1.80 (br, s, H-15), 1.38 (s, H-13), 1.35 (s, H-14); 4-aminophenylbutanoyl 2.53 (br, t, J 7 Hz, H-α), 1.80 (m, H-β), 2.25 (t, J 7 Hz, H-γ), 7.18 (H-2 and H-6), 7.05 (H-3 and H-5); boc 1.50 ($CH_3$). $^{13}C$ NMR ($CDCl_3$) δ: The guaianolide nucleus 58.1 (C-1), 76.7 (C-2), 84.0 (C-3), 141.2 (C-4), 130.3 (C-5), 77.5 (C-6), 78.4 (C-7), 66.7 (C-8), 38.0 (C-9), 84.6 (C-10), 78.3 (C-11), 175.6 (C-12), 15.7 (C-13), 22.5 (C-14), 12.8 (C-15); 4-aminophenylbutanoyl 172.4 (C=O), 33.3 (C-α and C-γ), 26.0 (C-β), 135.8 (C-1), 128.8 (C-2 and C-6), 119.0, (C-3 and C-5), 136.1 (C-4); boc 28.2 ($CH_3$), 80.5 (C—O), 152.8 (C=O). MS FAB found 840.4093. Calculated for $C_{45}H_{63}NO_{14}$, 840.4170.

A solution of 8-O-(4-[4-t-butoxycarbonylaminophenyl] butanoyl)-8-O-debutanoylthapsigargin (33.1 mg, 39 mM) and trifluoroacetic acid (TFA) (0.4 ml) in methylene chloride (4 ml) was then left for 0.75 hours at room temperature and concentrated in vacuo. ABuT (27.7 mg, 96%) was isolated from the residue as an amorphous powder by column chromatography using an eluent consisting of toluene-ethyl acetate-acetic acid (2:1:0.01) to which increasing amounts of ethyl acetate were added. $^1H$ NMR ($CDCl_3$) δ guaianolide 4.25 (br, s, H-1), 5.47 (br, t, J 2 Hz, H-2), 5.59 (t, J 3 Hz, H-3), 5.68 (s, H-6), 5.63 (br, s, H-8), 2.97 (dd, J 20 and 3 Hz, H-9), 1.84 (br, s, H-15), 1.40 (s, H-13), 1.37 (s, H-14); 4-aminophenylbutanoyl 2.52 (t, J 9 Hz, H-α), 2.24 (t, J 9 Hz, H-γ), 1.80 (m, H-β), 6.94 (d, J 7 Hz, H-2 and H-6), 6.64 (H-3 and H-5). $^{13}C$ NMR ($CDCl_3$) δ The guaianolide nucleus 57.5 (C-1), 76.7 (C-2), 84.1 (C-3), 141.6 (C-4), 130.5 (C-5), 77.8 (C-6), 78.5 (C-7), 66.1 (C-8), 38.1 (C-9), 84.6 (C-10), 78.5 (C-11), 178.5 (C-12), 15.7 (C-13), 22.5 (C-14), 12.8 (C-15); 4-aminophenylbutanoyl 172.7 (C=O), 34.0 (C-a), 33.6 (C-g), 26.9 (C-a), 129.3 (C-1), 129.3 (C-2 and C-6), 115.7, (C-3 and C-5), 143.9 (C-4). MS $FAB^-$ found 740.3672. Calculated for $C_{40}H_{55}NO_{12}$, 740.3646.

Example 16
Cytotoxicity and SERCA Inhibition Assays

Percentage clonogenic survival of TSU-Pr1 ($2 \times 10^5$ cells) following 72 hours of exposure to varying concentrations of TG analogs was performed as described in Martikainen et al. Cancer Res., 51, 4693–4700 (1991).

The inhibitory potency of thapsigargin and its analogs was determined as the concentration required to produce 50% inhibition (i.e. $IC_{50}$) of $^{45}Ca^+$ uptake to sarcoplasmic reticulum (SR) vesicles prepared from rabbit skeletal muscle by the method of De Meis and Hasselbach (J. Biol. Chem., 246: 4759–4763, 1971). The $^{45}Ca^{2+}$ uptake assay was as described previously (Christensen, et al., FEBS, 335: 345–348, 1993), with the following modifications: 5 μg/ml of SR protein was incubated at 25 EC and free $Ca^{2+}$ adjusted to 100 nM using 4 min. uptake time. Under these conditions, $Ca^{2+}$ could proceed linearly with time for at least 8 minutes. Measurements of $Ca^{2+}$ within TSU cells was determined as described previously (Lin et al., The Prostate, 33:201–207, 1997).

TABLE 5

| thapsigargin analog symbol | (IC$_{50}$ in nM) | (LC$_{50}$ in μM) |
|---|---|---|
| dBTG | 149 ± 21 | >10 |
| SDT | 1279 ± 91 | >25 |
| GDT | 316 ± 23 | 16.6 ± 0.4 |
| PDT | 17.7 ± 2.4 | 3.1 ± 0.2 |
| ABT-boc | ND | 12.0 ± 0.3 |
| ABT | 18.4 ± 0.3 | 4.0 ± 0.3 |
| AAT-boc | ND | >10 |
| AAT | ND | >10 |
| APT-boc | 21.2 ± 0.8 | 0.87 ± 0.015 |
| APT | 16.2 ± 0.9 | 0.275 ± 0.06 |
| ABuT-boc | 14.4 ± 0.8 | ND |
| ABuT | 18.4 ± 1.4 | 0.225 ± 0.02 |
| ACT-boc | 20.3 ± 0.2 | 1.9 ± 0.1 |
| ACT | 18.7 ± 0.2 | 0.10 ± 0.006 |
| TG | 5.0 ± 0.3 | 0.03 ± 0.004 |

The IC$_{50}$ results are mean (n = 3) ± standard error.
The LC$_{50}$ results are mean (n = 5) ± standard error.
The entry "ND" stands for "not determined".
Clonogenic survival not determined above 10 μM for dBTG.
Analogs with -boc have a t-butoxycarbonyl (boc) protected amino group.

Example 17
Toxicity of Doxorubicin Prodrug

The androgen responsive LNCaP and androgen independent TSU-Pr1 are human prostate cancer lines were obtained from ATCC (Rockville, Md.) and maintained by serial passage in RPMI 1640 media containing 10% fetal calf serum with 100 units/ml penicillin G, and 100 units/ml streptomycin sulfate (antibiotics from M.A. Bioproducts, Walkerville, Md.) as standard media in 5% CO$_2$/95% air at 37° C. The origins and characteristics of the LNCaP and TSU-Pr1 cell lines are described in Horoszewicz, et al., Cancer Res., 43:1809–1818, (1980)and Iizumi, et al., J. Urol., 137: 1304–1306, (1987).

To collect PSA to assay enzymatic activity, LNCaP cells were grown in standard media to 70–80% confluence. The serum containing media was then removed, cells washed twice with Hank's balanced salt solution and then new serum free media added that consisted of RPMI 1640 containing antibiotics and 100 nM dihydrotestosterone (DHT). PC-82 androgen dependent human prostate cancer xenografts were maintained by serial passage in athymic nude mice (Charles River). The origins and characteristics of this xenograft have been described in Hoehn, et al., Prostate 1:94–104, (1980). Primary cultures of PC-82 were established as described in Berges, et al., Clin. Cancer. Res., 1:473–480, (1995).

Substrate hydrolysis was studied by measuring fluorescence change secondary to AMC release as described in Example 1.

PSA concentration in conditioned tissue culture media was determined using the Tandem-R PSA assay (Hybritech, San Diego, Calif.) according to the manufacturer's instructions. Samples were then diluted to equivalent PSA concentrations in PSA assay buffer. PSA immunoprecipitation was then performed using the mouse monoclonal anti-PSA antibody H117 that recognizes both free PSA and PSA complexed to α-antichymotrypsin as described in Denmeade et al., Cancer Res., 57:4920–4926, (1997).

Conditioned media from LNCaP cells containing the doxorubicin prodrug was applied to C$_{18}$ reversed phase Bond-Elut column (Varian, Carpinteria, Calif.) and washed with 3 ml of buffer (i.e. 6 column volumes) consisting of 0.1 M phosphoric acid and 5% acetonitrile in PBS as described in DeJong, et al., J. Clin. Onc., 10:1897–1906, (1992). Samples were eluted from the column using 2 ml of a solution of 70% acetonitrile/0.1% TFA (vol/vol). The solvents were then evaporated to dryness and the samples were redissolved in 0.1% TFA (vol/vol) and applied to the HPLC column.

The HPLC system consisted of a dual-pump (Model 126, Beckman Instruments, Columbia, Md.) with a manual injection valve (Rheodyne, Cotati, Calif.) fitted with a 1 ml injection loop. A reversed phase C$_{18}$ Ultrasphere analytical column (Beckman) 15 cm×4.6 mm (I.D.) was used together with a 4.5 cm×4.6 mm (I.D.) Ultrasphere reversed phase guard column (Beckman). A gradient elution was performed consisting of eluent A, 0.1% TFA (vol/vol) and eluent B, 70% acetonitrile/0.1% TFA (vol/vol) with a gradient of 0–30% B over 5 min then 30–60% B over 25 min. with a flow rate of 1 ml/min. A diode arTay detector (Model 168, Beckman) was used to monitor the effluent at 480 nm. All analyses were conducted at ambient temperature. Data processing was performed using Gold Chromatography Data System, version 1.0 (Beckman).

Percentage clonogenic survival of TSU-Pr1 (2×10$^5$ cells) following 48 hr. exposure to varying concentrations of doxorubicin prodrugs with or without exogenously added PSA was performed as described in Martikainen et al., Cancer Res., 51:4693–4700, (1991).

To analyze the cytotoxicity of the doxorubicin prodrugs against LNCAP cells, these cells were exposed to varying concentrations of prodrugs for 72 hours. Cells were then counted and the percent viable cells determined by Trypan Blue exclusion using a hemocytometer. The dose that produced 50% cytotoxicity as compared to controls was then determined [i.e. the lethal dose$_{50}$ (LD$_{50}$)] for both LNCaP and TSU cells.

The Mu-HSSKLQ-(SEQ ID NO: 7)-AMC substrate was custom synthesized by Enzyme Systems Products (Dublin, Calif.) and characterized as described in Denmeade et al., Cancer Res., 57:4920–4926, (1997). Doxorubicin (Dox) prodrugs [Ac-His-Ser-Ser-Lys-Leu-Gln(SEQ ID NO: 3)-Dox is (HSSKLQ-Dox) where Ac is acetyl] and [His-Ser-Ser-Lys-Leu-Gln-Leu-(SEQ ID NO: 14) Dox (Mu-HSSKLQ-Leu-Dox) where Mu is morpholinocarbonyl] were synthesized by coupling the primary amine of doxorubicin to the carboxyl group of the C-terminal amino acid. Purification of both compounds by HPLC yielded the trifluoroacetate salt (>98% purity). The peptide sequence was confirmed by amino acid analysis and molecular weights were No confirmed by mass spectroscopy.

Doxorubicin was from Pharmacia, (Kalamazoo, Mich.). L-Leucyldoxorubicin was provided synthesized by A.N. PSA was purified from human seminal plasma as described in Lilja et al., Clin. Chem., 37:1618, (1991). α1-antichymotrpsin and α$_2$-macroglobulin and other reagents were obtained from Sigma Chemical Co.(St. Louis, Mo.). Mouse monoclonal IgG anti-PSA antibodies H117 and 5A10 were described previously in Lövgren et al., Biochem. Biophys. Res. Comm., 213:888–895, (1995).

Table 6 shows the clonogenic survival of TSU-Pr1 cells following 48 hours of treatment with Mu-His-Ser-Ser-Lys-Leu-Gln-Leu(SEQ ID NO: 14)-doxorubicin prodrug with and without 30 µg/ml enzymatically active PSA. Results for Mu-His-Ser-Ser-Lys-Leu-Gln(SEQ ID NO: 7)-doxorubicin at 50 µM, were 122 colonies for treatment without PSA, and 110 colonies for treatment with 30 µg/m, enzymatically active PSA. Results are shown as averages (n 5) with standard error of 2 to 7. Assays were done in triplicate.

TABLE 6

| Mu-HSSKLQ (SEQ ID NO: 14) Leu-Doxorubicin (nM) | number of TSU-Pr1 colonies after 48 hours treatment | |
| --- | --- | --- |
| | without PSA | with PSA (30 µg/ml) |
| 0 | 130 | 107 |
| 50 | 110 | 90 |
| 100 | 127 | 87 |

TABLE 6-continued

| Mu-HSSKLQ (SEQ ID NO: 14) Leu-Doxorubicin (nM) | number of TSU-Pr1 colonies after 48 hours treatment | |
| --- | --- | --- |
| | without PSA | with PSA (30 µg/ml) |
| 250 | 123 | 50 |
| 500 | 117 | 18 |
| 1000 | 118 | 10 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A peptide comprising an amino acid sequence having a cleavage site specific for an enzyme having a proteolytic activity of prostate specific antigen, wherein the peptide is 20 or fewer amino acids in length, and wherein the sequence comprises the amino acids $X_5 X_4 X_3 X_2 X_1$, wherein $X_5$ is from 0 to 16 amino acids; $X_4$ is serine, isoleucine, or lysine; $X_3$ is serine or lysine; $X_2$ is leucine or lysine; and $X_1$ is glutamine, asparagine or tyrosine.

2. The peptide of claim 1, further comprising $X_{-1}$ linked to $X_1$, wherein $X_{-1}$ is from 1 to 10 amino acids.

3. The peptide of claim 1, wherein $X_1$ is glutamine.

4. The peptide of claim 1, further comprising amino acid $X_6$ linked to the amino terminus of $X_5$, wherein $X_6$ is from 0 to 15 amino acids and wherein $X_5$ is serine or lysine.

5. The peptide of claim 4, further comprising amino acid $X_7$ linked to the amino terminus of $X_6$, wherein $X_7$ is from 0 to 14 amino acids and wherein $X_6$ is histidine or asparagine.

6. The peptide of claim 2, wherein $X_{-1}$ comprises leucine.

7. The peptide of claim 6, wherein the amino acid sequence is selected from the group consisting of His-Ser-Ser-Lys-Leu-Gln, and Glu-His-Ser-Ser-Lys-Leu-Gln.

8. The peptide of claim 1, further comprising a capping group attached to the N-terminus of the peptide, the group inhibiting endopeptidase activity on the peptide.

9. The peptide of claim 8, wherein the capping group is selected from the group consisting of acetyl, morpholinocarbonyl, benzyloxycarbonyl, glutaryl and succinyl substituents.

10. The peptide of claim 1, wherein the cleavage of the peptide by the enzyme yields at least 5 picomoles of cleaved peptide per minute per 200 picomoles of enzyme.

11. The peptide of claim 1, wherein the cleavage of the peptide in human serum yields at most 2.0 picomoles of cleaved peptide per minute.

12. A peptide of claim 1, further comprising an added substituent which renders the peptide water-soluble.

13. A peptide of claim 12, wherein the added substituent is a polysaccharide.

14. A peptide of claim 13, wherein the polysaccharide is selected from the group consisting of modified or unmodified dextran, cyclodextrin, and starch.

15. A peptide of claim 1, further comprising an antibody attached to the amino terminus of $X_5$, or $X_4$ when $X_5$ is 0.

16. A peptide composition comprising a plurality of peptides, each peptide comprising an amino acid sequence having a cleavage site specific for an enzyme having a proteolytic activity of prostate specific antigen, wherein each peptide has 20 or fewer amino acids, and wherein the sequence comprises the amino acids $X_5 X_4 X_3 X_2 X_1$, wherein $X_5$ is from 0 to 16 amino acids; $X_4$ is serine, isoleucine, or lysine; $X_3$ is serine or lysine; $X_2$ is leucine or lysine; and $X_1$ is glutamine, asparagine or tyrosine.

17. The peptide of claim 1, further comprising a peptide toxin attached to the amino terminus of $X_5$, or $X_4$ when $X_5$ is 0.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO:1:

Ser Lys Leu Gln
 1

(2) INFORMATION FOR SEQ ID NO:2:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO:2:

Ile Ser Tyr Gln
 1

(2) INFORMATION FOR SEQ ID NO:3:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (xi) SEQUENCE DESCRIPTION: SEQ ID NO:3:

```
Lys Ser Lys Gln
  1

(2) INFORMATION FOR SEQ ID NO:4:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:4:

Ser Ser Lys Leu Gln
  1               5

(2) INFORMATION FOR SEQ ID NO:5:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:5:

Lys Ile Ser Tyr Gln
  1               5

(2) INFORMATION FOR SEQ ID NO:6:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:6:

Thr Lys Ser Lys Gln
  1               5

(2) INFORMATION FOR SEQ ID NO:7:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:7:

His Ser Ser Lys Leu Gln
  1               5

(2) INFORMATION FOR SEQ ID NO:8:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:8:

Asn Lys Ile Ser Tyr Gln
  1               5
```

(2) INFORMATION FOR SEQ ID NO:9:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:9:

Ala Thr Lys Ser Lys Gln
 1          5

(2) INFORMATION FOR SEQ ID NO:10:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:10:

Glu His Ser Ser Lys Leu Gln
 1          5

(2) INFORMATION FOR SEQ ID NO:11:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:11:

Gln Asn Lys Ile Ser Tyr Gln
 1          5

(2) INFORMATION FOR SEQ ID NO:12:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:12:

Glu Asn Lys Ile Ser Tyr Gln
 1          5

(2) INFORMATION FOR SEQ ID NO:13:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:13:

Ala Thr Lys Ser Lys Gln His
 1          5

(2) INFORMATION FOR SEQ ID NO:14:

(i) SEQUENCE CHARACTERISTICS:
        (A) LENGTH: 7 amino acids

```
        (B) TYPE: amino acid
        (D) TOPOLOGY: linear (ii) MOLECULE TYPE: peptide (xi) SEQUENCE DESCRIPTION: SEQ ID NO:14:

His Ser Ser Lys Leu Gln Leu
 1               5
```